United States Patent
Dodd et al.

(10) Patent No.: US 11,407,735 B2
(45) Date of Patent: Aug. 9, 2022

(54) CRYSTALLINE FORMS OF N-[4-(CHLORODIFLUOROMETHOXY) PHENYL]-6-[(3R)-3-HYDROXY-PYRROLIDIN-1-YL]-5-(1H-PYRAZOL-5-YL)PYRIDINE-3-CARBOXAMIDE

(71) Applicant: NOVARTIS AG, Basel (CH)

(72) Inventors: Stephanie Kay Dodd, Ayer, MA (US); Arnaud Grandeury, Helfrantzkirch (FR); Emmanuel Suffert, Basel (CH); Evgenia Rousaki, Basel (CH)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 16/874,622

(22) Filed: May 14, 2020

(65) Prior Publication Data

US 2020/0361904 A1 Nov. 19, 2020

Related U.S. Application Data

(60) Provisional application No. 62/949,599, filed on Dec. 18, 2019, provisional application No. 62/848,857, filed on May 16, 2019.

(51) Int. Cl.
*C07D 401/14* (2006.01)
*A61K 9/20* (2006.01)

(52) U.S. Cl.
CPC .............. *C07D 401/14* (2013.01); *A61K 9/20* (2013.01); *C07B 2200/13* (2013.01)

(58) Field of Classification Search
CPC ...... C07D 401/14; A61K 9/20; C07B 2200/13
See application file for complete search history.

(56) References Cited

U.S. PATENT DOCUMENTS

| 2017/0216289 A1 | 8/2017 | Pendergast |
| 2019/0374618 A1 | 12/2019 | Krause et al. |

FOREIGN PATENT DOCUMENTS

| EP | 3120851 A1 | 1/2017 |
| EP | 3292870 A1 | 3/2018 |
| EP | 3509626 A1 | 7/2019 |
| WO | 2013171639 A1 * | 11/2013 |
| WO | WO2013171642 A1 | 11/2013 |
| WO | WO2016100882 A1 | 6/2016 |
| WO | WO2017013160 A1 | 1/2017 |
| WO | WO2018046666 A1 | 3/2018 |
| WO | WO2018060843 A1 | 4/2018 |
| WO | WO2019084499 A1 | 5/2019 |
| WO | WO2019232244 A2 | 12/2019 |

OTHER PUBLICATIONS

Tran, Phi et al; Disposition of asciminib, a potent BCR-ABL1 Tyrosine kinase inhibitor, in healthy male subjects, Novartis Pharmaceuticals Corporation, Xenobiotica (2020) 50(2), 160-179.

Menssen, Hans D., et al, Relative Bioavailability and Food Effect Evaluation for 2 Tablet Formulations of Asciminib in a 2-Arm Crossover, Randomized, Open-Label; Study in Healthy Volunteers, Novartis Pharma AG, Clinical Pharmacology in Drug Development (2019), 8(3), 385-394.

Elrashedy, Ahmed A. et al, The Perplexity of Synergistic Duality: Inter-molecular Mechanisms of Communication in BCR-ABL1; Anti-Cancer Agents in Medicinal Chemistry (2019), 19(13), 1642-1650.

Hughes, T.P., et al, Asciminib in chronic myeloid leukemia after ABL kinase inhibitors failure; New England Journal of Medicine (2019), 381(24), 2315-2326.

Manley, Paul W., et al, Progress in the discovery of BCR-ABL kinase inhibitors for the treatment of leukemia, Topics in Medicinal Chemistry (2018), 28(Cancer II), 1-37.

Zanforlin, Enrico, et al, A Chemical Approach to Overcome Tyrosine Kinase Inhibitors Resistance:Learning from Chronic Myeloid Leukemia, Current Medicinal Chemistry (2019), 26(33), 6033-6052.

Singh, Anand P., et al, Ponatinib-induced cardiotoxicity: delineating the signalling mechanisms and potential rescue strategies. Cardiovascular Research (2019), 115(5), 966-977.

Eide, Christopher A., et al, Combining the Allosteric Inhibitor Asciminib with Ponatinib Suppresses Emergence of and Restores Efficacy against Highly Resistant BCR-ABL1 Mutants, Cancer Cell (2019), 36(4), 431-443.e5.

El Rashedy, Ahmed A, et al.,A Synergistic Combination Against Chronic Myeloid Leukemia: An Intra-molecular Mechanism of Communication in BCR-ABL1 Resistance, Molecular Biocomputation and Drug Design Lab, School of Health Sciences, University of KwaZulu-Natal, Durban, 4001. S. Afr. Protein Journal (2019), 38(2), 142-150.

Zhan, Jiu-Yu, et al., Molecular Dynamics Investigation on the Asciminib Resistance Mechanism of I502L and V468F Mutations in BCR-ABL, Journal of Molecular Graphics & Modelling (2019), 89, 242-249.

Madhi,Raed, et al., c-Abl kinase regulates neutrophil extracellular trap formation, inflammation, and tissue damage in severe acute pancreatitis, Journal of Leukocyte Biology (2019),106(2), 455-466.

Inoue, Ai, et al., Chronic myeloid leukemia stem cells and molecular target therapies for overcoming resistance and disease persistence, International Journal of Hematology (2018), 108(4), 365-370.

Massaro, Fulvio et al., Novel tyrosine-kinase inhibitors for the treatment of chronic myeloid leukemia: safety and efficacy, Expert Review of Hematology (2018), 11(4), 301-306.

Qiang, W., et al, Mechanisims of resistance to the BCR-ABL1 allosteric inhibitor asciminib, Leukemia (2017), 31(12), 2844-2847.

\* cited by examiner

*Primary Examiner* — Paul V Ward
*Assistant Examiner* — Ebenezer O Sackey
(74) *Attorney, Agent, or Firm* — Scott W. Reid

(57) ABSTRACT

The present invention describes specific crystalline forms of N-[4-(Chlorodifluoromethoxy)phenyl]-6-[(3R)-3-hydroxypyrrolidin-1-yl]-5-(1H-pyrazol-5 -yl)pyridine-3-carboxamide. The present invention further relates to methods for preparing said crystalline forms, pharmaceutical compositions comprising said crystalline forms, and methods of using said crystalline forms and pharmaceutical compositions to treat disease.

10 Claims, 14 Drawing Sheets

CRYSTALLINE FORMS OF N-[4-(CHLORODIFLUOROMETHOXY)PHENYL]-6-[(3R)-3-HYDROXYPYRROLIDIN-1-YL]-5-(1H-PYRAZOL-5-YL)PYRIDINE-3-CARBOXAMIDE

CROSS-REFERENCE TO RELATED APPLICATIONS

This application claims the benefit of U.S. Provisional Patent Application Number 62/949599 filed 18 Dec. 2019 and U.S. Provisional Patent Application Number 62/848857 filed 16 May 2019. The full disclosures of these applications are incorporated herein by reference in their entirety and for all purposes.

FIELD OF THE INVENTION

The present invention is directed to crystalline forms of N-[4-(Chlorodifluoromethoxy)phenyl]-6-[(3R)-3-hydroxypyrrolidin-1-yl]-5-(1H-pyrazol-5-yl)pyridine-3-carboxamide, methods of making the same, pharmaceutical compositions comprising the same and methods of treatment using the same.

BACKGROUND

Polymorphism denotes the existence of more than one crystalline form of a substance. Polymorphs (or crystalline modifications) have an identical chemical structure but often quite different physicochemical properties. Polymorphs include enantiotropic polymorphs and monotropic polymorphs. This ability of a chemical substance to crystallize in more than one crystalline form can have a profound effect on the shelf life, solubility, formulation properties, and processing properties of a drug. In addition, the action of a drug can be affected by the polymorphism of the drug molecule. Different polymorphs can have different rates of uptake in the body, leading to lower or higher biological activity than desired. In extreme cases, an undesired polymorph can even show toxicity. The occurrence of an unknown crystalline form during manufacture can have a significant impact.

Understanding and controlling polymorphism, then, gives a decided advantage in bringing new drugs to the marketplace. First and foremost, searching for any possible polymorphs for a drug product can be used to diminish the possibility of contamination during a drug's manufacture or storage by other polymorphic forms. Failure to catch contamination can have life-threatening consequences in some cases. Crystallizing an unintended polymorph during manufacture can mean weeks or even months of production downtime while scientists find and correct the cause of the new crystalline form or go through another round of testing to obtain approval for the new crystalline form.

Second, understanding which crystalline forms of a drug are possible in certain cases allows researchers to maximize the desired properties of a compound, such as solubility, formulation properties, processing properties, and shelf life. Understanding these factors early in the development of a new drug may mean a more active, more stable, or less expensively manufactured drug.

The compound N-[4-(Chlorodifluoromethoxy)phenyl]-6-[(3R)-3-hydroxypyrrolidin-1-yl]-5-(1H-pyrazol-5-yl)pyridine-3-carboxamide of the formula

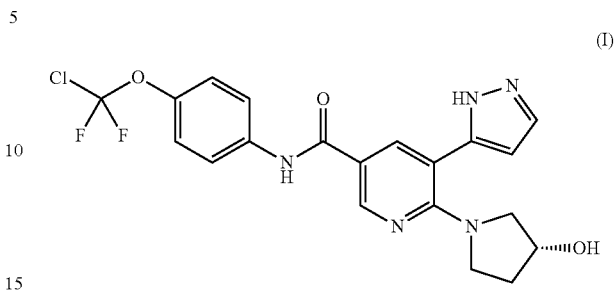

(I)

is a BCR-ABL tyrosine-kinase inhibitor. The compound of Formula (I), preparation of the compound of Formula (I), and pharmaceutical compositions of the compound of Formula (I) are originally described in WO 2013/171639 A1 as Example 9. The compound of Formula (I) is also known as (R)—N-(4-(chlorodifluoromethoxy)phenyl)-6-(3-hydroxypyrrolidin-1-yl)-5-(1H-pyrazol-5-yl)nicotinamide, or asciminib.

WO 2013/171639 A1 provides that the Compound of Formula (I) as useful in treating diseases which respond to inhibition of the tyrosine kinase enzymatic activity of the Abelson protein (ABL1), the Abelson-related protein (ABL2) and related chimeric proteins, in particular BCR-ABL1. While WO 2013/171639 Al describes a pharmaceutical composition comprising an amorphous dispersion of N-[4-(Chlorodifluoromethoxy)phenyl]-6-[(3R)-3-hydroxypyrrolidin-1-yl]-5-(1H-pyrazol-5-yl)pyridine-3-carboxamide, it does not particularly disclose of any crystalline forms of N-[4-(Chlorodifluoromethoxy)phenyl]-6-[(3R)-3-hydroxypyrrolidin-1-yl]-5-(1H-pyrazol-5-yl)pyridine-3-carboxamide or pharmaceutical formulations comprising the same.

Crystalline forms of N-[4-(Chlorodifluoromethoxy)phenyl]-6-[(3R)-3-hydroxypyrrolidin-1-yl]-5-(1H-pyrazol-5-yl)pyridine-3-carboxamide have been discovered and exhibit new physical properties that may be exploited in order to obtain new pharmacological properties, and that may be utilized in the drug product development of N-[4-(Chlorodifluoromethoxy)phenyl]-6-[(3R)-3-hydroxypyrrolidin-1-yl]-5-(1H-pyrazol-5-yl)pyridine-3-carboxamide.

SUMMARY OF THE INVENTION

The present invention is directed to crystalline forms of N-[4-(Chlorodifluoromethoxy)phenyl]-6-[(3R)-3-hydroxypyrrolidin-1-yl]-5-(1H-pyrazol-5-yl)pyridine-3-carboxamide free base.

The present invention is also directed to crystalline forms of the hydrochloride salt of N-[4-(Chlorodifluoromethoxy)phenyl]-6-[(3R)-3-hydroxypyrrolidin-1-yl]-5-(1H-pyrazol-5-yl)pyridine-3-carboxamide.

The present invention also provides a pharmaceutical composition comprising: (a) a therapeutically effective amount of a crystalline form of N-[4-(Chlorodifluoromethoxy)phenyl]-6-[(3R)-3-hydroxypyrrolidin-1-yl]-5-(1H-pyrazol-5-yl)pyridine-3-carboxamide free base or hydrochloride salt thereof of the present invention; and (b) at least one pharmaceutically acceptable carrier.

The present invention is also directed to a method for treating an ABL1/BCR-ABL1-mediated disorder comprising the step of administering to a subject in need of such treatment a therapeutically effective amount of a crystalline form of N-[4-(Chlorodifluoromethoxy)phenyl]-6-[(3R)-3- hydroxypyrrolidin-1-yl]-5-(1H-pyrazol-5-yl)pyridine-3-carboxamide free base or hydrochloride salt thereof of the present invention.

DETAILED DESCRIPTION OF THE INVENTION

Figure 1:
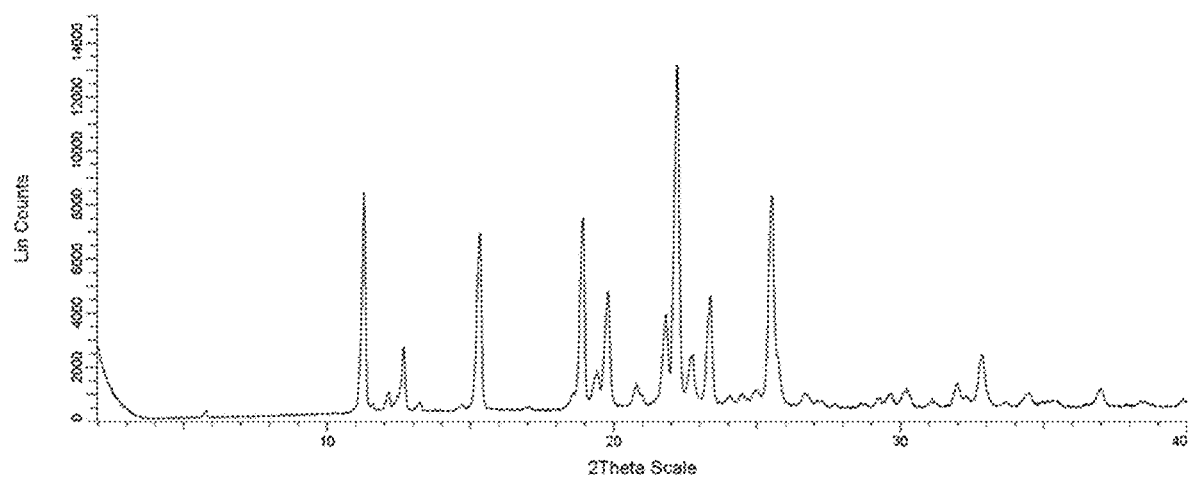
FIG. 1 depicts the X-ray powder diffraction (XRPD) pattern for crystalline form A of N-[4-(Chlorodifluoromethoxy)phenyl]-6-[(3R)-3-hydroxypyrrolidin-1-yl]-5-(1H-pyrazol-5-yl)pyridine-3-carboxamide free base according to the present invention.

In the context of the present invention, the following definitions have the indicated meaning, unless explicitly stated otherwise:

As used herein the term "room temperature" or "RT" refers to a temperature in the range of from 20 to 30° C.

The term "reflection" with regard to X-ray powder diffraction (XRPD) as used herein, means peaks in an X-ray diffractogram, which are caused at certain diffraction angles (Bragg angles) by constructive interference from X-rays scattered by parallel planes of atoms in solid material, which are distributed in an ordered and repetitive pattern in a long-range positional order. Such a solid material is classified as crystalline material, whereas amorphous material is defined as solid material, which lacks long-range order and only displays short-range order, thus resulting in broad scattering. According to literature, long-range order e.g. extends over approximately 100 to 1000 atoms, whereas short-range order is over a few atoms only (see "*Fundamentals of Powder Diffraction and Structural Characterization of Materials*" by Vitalij K. Pecharsky and Peter Y. Zavalij, Kluwer Academic Publishers, 2003, page 3).

The crystalline forms of the present invention may be referred to herein as being characterized by graphical data "as shown in" a figure, for example, XRPD. The person skilled in the art understands that factors such as variations in instrument type, response and variations in sample directionality, sample concentration and sample purity may lead to small variations for such data when presented in graphical form, for example variations relating to the exact peak positions and intensities. However, a comparison of the graphical data in the figures herein with the graphical data generated for another or an unknown solid form and the confirmation that two sets of graphical data relate to the same crystal form is well within the knowledge of a person skilled in the art.

The terms "solid form" or "solid state form" as used herein interchangeably refer to any crystalline and/or amorphous phase of a compound.

As used herein, the term "amorphous" refers to a solid form of a compound that is not crystalline. An amorphous compound possesses no long-range order and does not display a definitive XRPD pattern with reflections.

As used herein the term "polymorph" refers to crystalline forms having the same chemical composition but different spatial arrangements of the molecules, atoms, and/or ions forming the crystal.

The term "hydrate" as used herein, refers to a crystalline solid where either water is cooperated in or accommodated by the crystal structure, e.g., is part of the crystal structure or entrapped into the crystal (water inclusions). Thereby, water can be present in a stoichiometric or non-stoichiometric amount. When water is present in stoichiometric amount, the hydrate may be referred to by adding Greek numeral prefixes. For example, a hydrate may be referred to as a hemihydrate or as a monohydrate depending on the water/compound stoichiometry. The water content can be measured, for example, by Karl-Fischer-Coulometry.

The terms "dehydrating" or "dehydration" as used herein, describe the at least partial removal of water from the crystal structure of the host molecule.

The term "solvate" as used herein, refers to a crystalline solid were either one or more organic solvent(s) is/are cooperated in or accommodated by the crystal structure e.g. is/are part of the crystal structure or entrapped into the crystal (water inclusions). Thereby, the one or more organic solvent(s) can be present in a stoichiometric or non-stoichiometric amount. When the one or more organic solvent(s) is/are present in stoichiometric amount(s), the solvate may be referred to by adding Greek numeral prefixes. For example, a solvate may be referred to as a hemisolvate or as a monosolvate depending on the solvent(s)/compound stoichiometry. The solvent content can be measured, for example, by GC, NMR, SXRD and/or TGA/MS.

The term "pharmaceutically acceptable excipient" as used herein refers to substances, which do not show a significant pharmacological activity at the given dose and that are added to a pharmaceutical composition in addition to the active pharmaceutical ingredient. Excipients may take the function of vehicle, diluent, release agent, disintegrating agent, dissolution modifying agent, absorption enhancer, stabilizer or a manufacturing aid among others. Excipients may include fillers (diluents), binders, disintegrants, lubricants and glidants.

The terms "filler" or "diluent" as used herein refer to substances that are used to dilute the active pharmaceutical ingredient prior to delivery. Diluents and fillers can also serve as stabilizers.

As used herein the term "binder" refers to substances that bind the active pharmaceutical ingredient and pharmaceutically acceptable excipient together to maintain cohesive and discrete portions.

The terms "disintegrant" or "disintegrating agent" as used herein refers to substances which, upon addition to a solid pharmaceutical composition, facilitate its break-up or disintegration after administration and permits the release of the active pharmaceutical ingredient as efficiently as possible to allow for its rapid dissolution.

The term "lubricant" as used herein refers to substances that are added to a powder blend to prevent the compacted powder mass from sticking to the equipment during tableting or encapsulation process. They aid the ejection of the tablet from the dies and can improve powder flow.

The term "glidant" as used herein refers to substances that are used for tablet and capsule formulations in order to improve flow properties during tablet compression and to produce an anti-caking effect.

One aspect of the present invention provides distinct crystalline forms of the free base and the hydrochloride salt of the compound N-[4-(Chlorodifluoromethoxy)phenyl]-6-[(3R)-3-hydroxypyrrolidin-1-yl]-5-(1H-pyrazol-5-yl)pyridine-3-carboxamide. These "crystalline form(s)" (or "crystal forms" or "crystalline modification(s)" or "polymorphic form(s)" or "polymorph(s)", as the terms will be used interchangeably herein) differ with respect to thermodynamic stability, physical parameters, x-ray structure and methods of preparation. Polymorphs exist in two main categories: enantiotropic or monotropic. "Enantiotropic" polymorphs are those that can interconvert depending upon the temperature at a given pressure or depending upon the pressure at a given temperature, called the transition temperature or pressure. The relative thermodynamic stability inverts above and below the transition temperature or pressure. If one polymorph is more stable independent of the temperature, it is "monotropic." While polymorphism classically refers to the ability of a compound to crystallize into more than one distinct crystal species (having identical chemical structure but quite different physicochemical properties), the term pseudopolymorphism is typically applied to solvate and hydrate crystalline forms. For purposes of this invention, however, both true polymorphs as well as pseudopolymorphs, i.e., hydrate and solvate forms, are included in the scope of "crystalline forms." In addition, "amorphous" refers to a disordered solid state. It should be noted that different samples of a particular crystalline form will share the same major X-ray powder diffraction (XRPD) "peaks" or "reflections," but that there can be variation in powder patterns with regard to minor peaks. In addition, the term "about" with regard to XRPD peak values (in degrees) generally means within 0.3°, more preferably within 0.2°, and most preferably within 0.1° of the given value. Alternatively, the term "about" means (in this and all contexts) within an accepted standard of error of the mean, when considered by one of ordinary skill in the art. As used herein, the term "substantially pure" means that more 50% of the crystalline N-[4-(Chlorodifluoromethoxy)phenyl]-6-[(3R)-3-hydroxypyrrolidin-1-yl]-5-(1H-pyrazol-5-yl)pyridine-3-carboxamide or hydrochloride salt thereof is present in one of the forms described herein and preferably at least 70%, more preferably at least 80%, and most preferably at least 90% of one of the crystalline forms described herein is present.

In one embodiment, a crystalline form of N-[4-(Chlorodifluoromethoxy)phenyl]-6-[(3R)-3-hydroxypyrrolidin-1-yl]-5-(1H-pyrazol-5-yl)pyridine-3-carboxamide is provided, referred to as crystalline form A of the free base. Form A of the free base is non-hygroscopic (exhibits less than 0.1% water uptake at 25° C. up to 92% relative humidity) and has rather low solubility above pH 3. As measured on a VanKel instrument using a Cary 100 photometer, the intrinsic dissolution rate of Form A was determined in pH 4.5, pH 6.8 and 0.1 N HCl medium as follows:

TABLE 1

Results of Intrinsic Dissolution of Free Base form A

| Dissolution medium | Intrinsic DR value [mg/min/cm2] |
|---|---|
| HCL 0.1N | 1.8; 1.9 |
| Acetate buffer pH 4.5 | n.a (does not dissolve) |
| pH = 6.8 | n.a (does not dissolve) |

In one embodiment, the invention relates to crystalline form A of N-[4-(Chlorodifluoromethoxy)phenyl]-6-[(3R)-3-hydroxypyrrolidin-1-yl]-5-(1H-pyrazol-5-yl)pyridine-3-carboxamide characterized by having a XRPD pattern comprising reflections at 2-Theta angles (2 theta values) of:
12.7±0.2°, 18.9±0.2° and 20.8±0.2°; or
12.7±0.2°, 15.3±0.2°, 18.9±0.2°, 20.8±0.2° and 25.0±0.2°; or
5.8°±0.2°, 11.3°±0.2°, 11.6°±0.2°, 12.2°±0.2°, 12.7°±0.2°, 13.2°±0.2°, 14.7°±0.2°, 15.3°±0.2°, 17.0°±0.2°, 17.4°±0.2°, 18.6°±0.2°, 18.9°±0.2°, 19.4°±0.2°, 19.8°±0.2°, 20.8°±0.2°, 21.8°±0.2°, 22.2°±0.2°, 22.7°±0.2°, 23.4°±0.2°, 24.0°±0.2°, 24.5°±0.2°, 25.0°±0.2°, 25.5°±0.2°, 26.7°±0.2°, 27.1°±0.2°, 27.7°±0.2°, 28.7°±0.2°, 29.3°±0.2°, 29.6°±0.2°, 30.2°±0.2°, 31.2°±0.2°, 32.0°±0.2°, 32.3°±0.2°, 32.8°±0.2°, 33.7°±0.2°, 34.5°±0.2°, 35.3°±0.2°, 37.0°±0.2°, 38.4°±0.2°, and 38.6°±0.2°, when measured at a temperature in the range of from 20 to 25° C. with Cu-Kalpha1,2 radiation having a wavelength of 0.1541 Å.

In another embodiment, crystalline form A of N-[4-(Chlorodifluoromethoxy)phenyl]-6-[(3R)-3-hydroxypyrrolidin-1-yl]-5-(1H-pyrazol-5-yl)pyridine-3-carboxamide is characterized by having a XRPD pattern comprising at least three, or at least four, or at least five, or all, 2 theta values selected from the group consisting of 5.8°, 11.3°, 11.6°, 12.2°, 12.7°, 13.2°, 14.7°, 15.3°, 17.0°, 17.4°, 18.6°, 18.9°, 19.4°, 19.8°, 20.8°, 21.8°, 22.2°, 22.7°, 23.4°, 24.0°, 24.5°, 25.0°, 25.5°, 26.7°, 27.1°, 27.7°, 28.7°, 29.3°, 29.6°, 30.2°, 31.2°, 32.0°, 32.3°, 32.8°, 33.7°, 34.5°, 35.3°, 37.0°, 38.4°, and 38.6° (2θ degrees±0.2°), when measured at a temperature in the range of from 20 to 25° C. with Cu-Kalpha1,2 radiation having a wavelength of 0.1541 Å.

In another embodiment of the present invention, crystalline form A of N-[4-(Chlorodifluoromethoxy)phenyl]-6-[(3R)-3-hydroxypyrrolidin-1-yl]-5-(1H-pyrazol-5-yl)pyridine-3-carboxamide free base is characterized by the XRPD pattern of FIG. 1.

Figure 2:
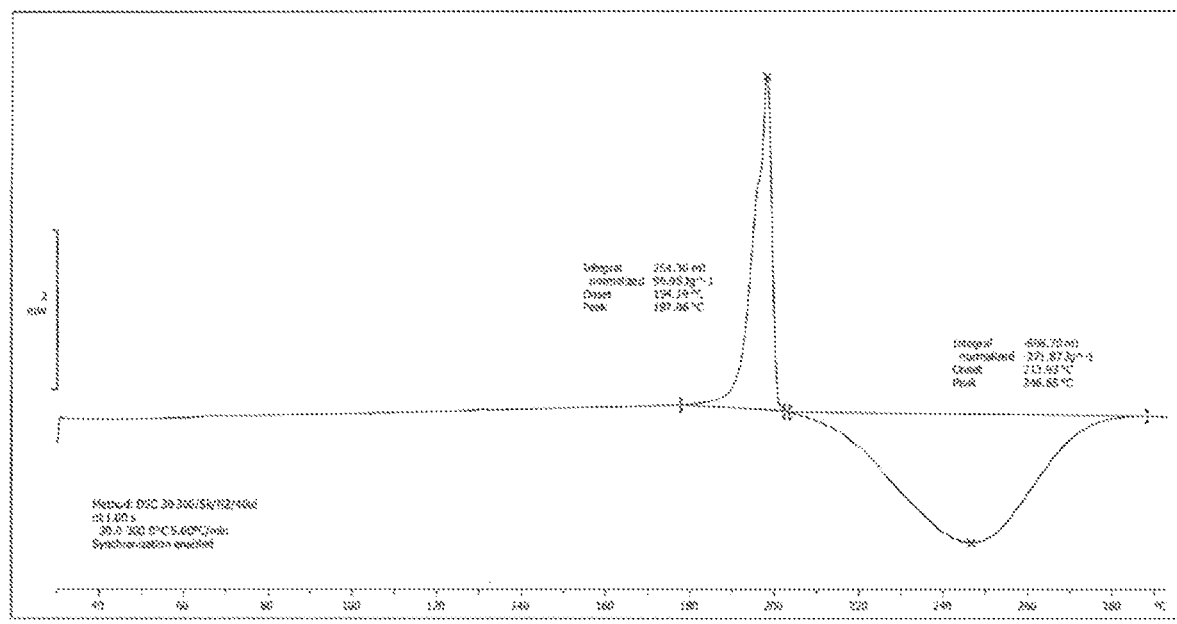
FIG. 2 depicts the differential scanning calorimetry curve for crystalline form A of N-[4-(Chlorodifluoromethoxy)phenyl]-6-[(3R)-3-hydroxypyrrolidin-1-yl]-5-(1H-pyrazol-5-yl)pyridine-3-carboxamide free base according to the present invention.
Figure 3:
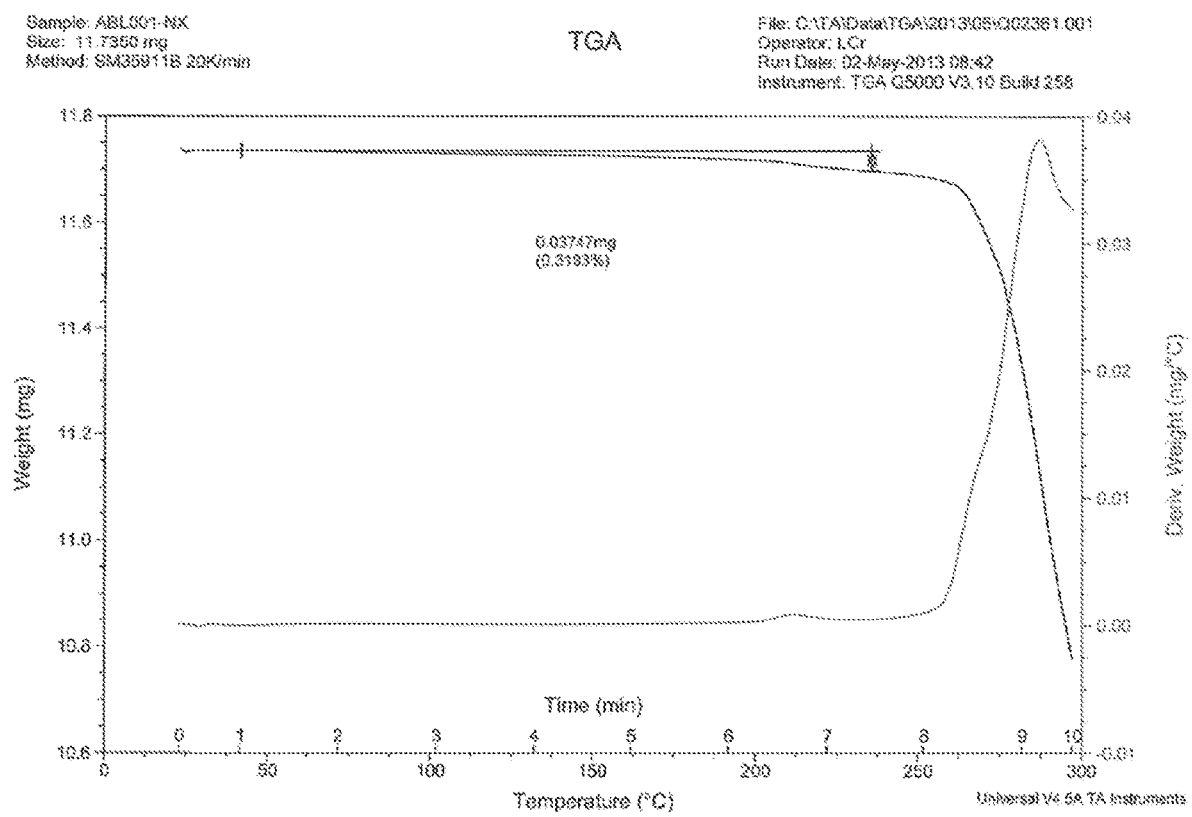
FIG. 3 depicts the thermogravimetric plot for crystalline form A of N-[4-(Chlorodifluoromethoxy)phenyl]-6-[(3R)-3-hydroxypyrrolidin-1-yl]-5-(1H-pyrazol-5-yl)pyridine-3-carboxamide free base according to the present invention.

Thermal properties of crystalline form A of N-[4-(Chlorodifluoromethoxy)phenyl]-6-[(3R)-3-hydroxypyrrolidin-1-yl]-5-(1H-pyrazol-5-yl)pyridine-3-carboxamide was analyzed by differential scanning calorimetry (DSC) at a scanning rate of 5° C./min. (FIG. 2) and thermogravimetric analysis (TGA) (FIG. 3).

In addition, several solvates were discovered during equilibration, crystallization, and precipitation studies of crystalline form A of N-[4-(Chlorodifluoromethoxy)phenyl]-6-[(3R)-3-hydroxypyrrolidin-1-yl]-5-(1H-pyrazol-5-yl)pyridine-3-carboxamide. A methanol solvate form $S_A$, a 1-propanol solvate form $S_B$, and an ethanol solvate form $S_C$ was isolated during equilibration and crystallization studies with the respective solvents. An acetone solvate form $S_D$ from was isolated in a precipitation study with acetone and water. Solvate forms $S_A$, $S_B$, $S_C$, and $S_D$ are characterized by the XRPD patterns shown in FIGS. 4-7, respectively.

In another embodiment, the invention relates to crystalline forms of the hydrochloride salt of N-[4-(Chlorodifluoromethoxy)phenyl]-6-[(3R)-3-hydroxypyrrolidin-1-yl]-5-(1H-pyrazol-5-yl)pyridine-3-carboxamide, referred to as crystalline forms A and B and trihydrate, Modification $H_A$. Forms A and B are enantiotropically related. Form A possesses greater physical stability at temperatures below the enantiotropic transition temperature range of 65° C. to 90° C. and Form B possess greater physical stability above this range. Form B spontaneously transforms to Form A at ambient conditions. Form A can be converted to Modification HA, or Form $H_A$, when equilibrated in water at pH 1.

Form A of the hydrochloride salt is non-hygroscopic (exhibits less than 0.4% water uptake at 25° C. up to 95% relative humidity) and has rather low solubility above pH 3. As measured on a VanKel instrument using a Cary 100 photometer, the intrinsic dissolution rate of Form A was determined in pH 3.5, pH 4.5 and 0.1 N HCl medium as follows:

TABLE 2

Results of Intrinsic Dissolution of form A of HCl salt

| Dissolution medium | Intrinsic DR value [mg/min/cm2] |
|---|---|
| HCL 0.1N (pH 1) | 0.16 |
| HCL 0.01N (pH 2) | 2.25 |
| Citrate buffer (pH 3.5) | 0.02 |
| Acetate buffer (pH 4.5) | 0.01 |

In another embodiment, the invention relates to crystalline form A of N-[4-(Chlorodifluoromethoxy)phenyl]-6-[(3R)-3-hydroxypyrrolidin-1-yl]-5-(1H-pyrazol-5-yl)pyridine-3-carboxamide hydrochloride characterized by having a XRPD pattern comprising reflections at 2-Theta angles (2 theta values) of:
12.6±0.2°, 18.9±0.2° and 20.9±0.2°; or
12.6±0.2°, 17.0±0.2°, 18.9±0.2°, 20.9±0.2° and 32.5 ±0.2°; or
8.5°±0.2°, 9.5°±0.2°, 11.8°±0.2°, 12.3°±0.2°, 12.6°±0.2°, 13.9°±0.2°, 14.8°±0.2°, 15.9°±0.2°, 16.5°±0.2°, 17.0°±0.2°, 17.6°±0.2°, 18.9°±0.2°, 19.1°±0.2°, 19.8°±0.2°, 20.4°±0.2°, 20.9°±0.2°, 21.2°±0.2°, 22.4°±0.2°, 22.7°±0.2°, 23.9°±0.2°, 24.3°±0.2°, 24.8°±0.2°, 25.0°±0.2°, 25.9°±0.2°, 26.8°±0.2°, 27.0°±0.2°, 28.3°±0.2°, 28.6°±0.2°, 28.9°±0.2°, 29.8°±0.2°, 30.5°±0.2°, 31.3°±0.2°, 31.5°±0.2°, 31.8°±0.2°, 32.1°±0.2°, 32.5°±0.2°, 32.9°±0.2°, 33.6°±0.2°, 34.0°±0.2°, 34.6°±0.2°, 35.0°±0.2°, 35.6°±0.2°, 36.3°±0.2° and 38.8°±0.2°, when measured at a temperature in the range of from 20 to 25° C. with Cu-Kalpha1,2 radiation having a wavelength of 0.1541 Å.

In another embodiment, the XRPD pattern of crystalline form A of N-[4-(Chlorodifluoromethoxy)phenyl]-6-[(3R)-3-hydroxypyrrolidin-1-yl]-5-(1H-pyrazol-5-yl)pyridine-3-carboxamide hydrochloride is characterized by at least three, or at least four, or at least five, or all, 2 theta values selected from the group consisting of 8.5°, 9.5°, 11.8°, 12.3°, 12.6°, 13.9°, 14.8°, 15.9°, 16.5°, 17.0°, 17.6°, 18.9°, 19.1°, 19.8°, 20.4°, 20.9°, 21.2°, 22.4°, 22.7°, 23.9°, 24.3°, 24.8°, 25.0°, 25.9°, 26.8°, 27.0°, 28.3°, 28.6°, 28.9°, 29.8°, 30.5°, 31.3°, 31.5°, 31.8°, 32.1°, 32.5°, 32.9°, 33.6°, 34.0°, 34.6°, 35.0°, 35.6°, 36.3°, 38.8° (2θ degrees±0.2°), when measured at a temperature in the range of from 20 to 25° C. with Cu-Kalpha1,2 radiation having a wavelength of 0.1541 Å.

Figure 8:
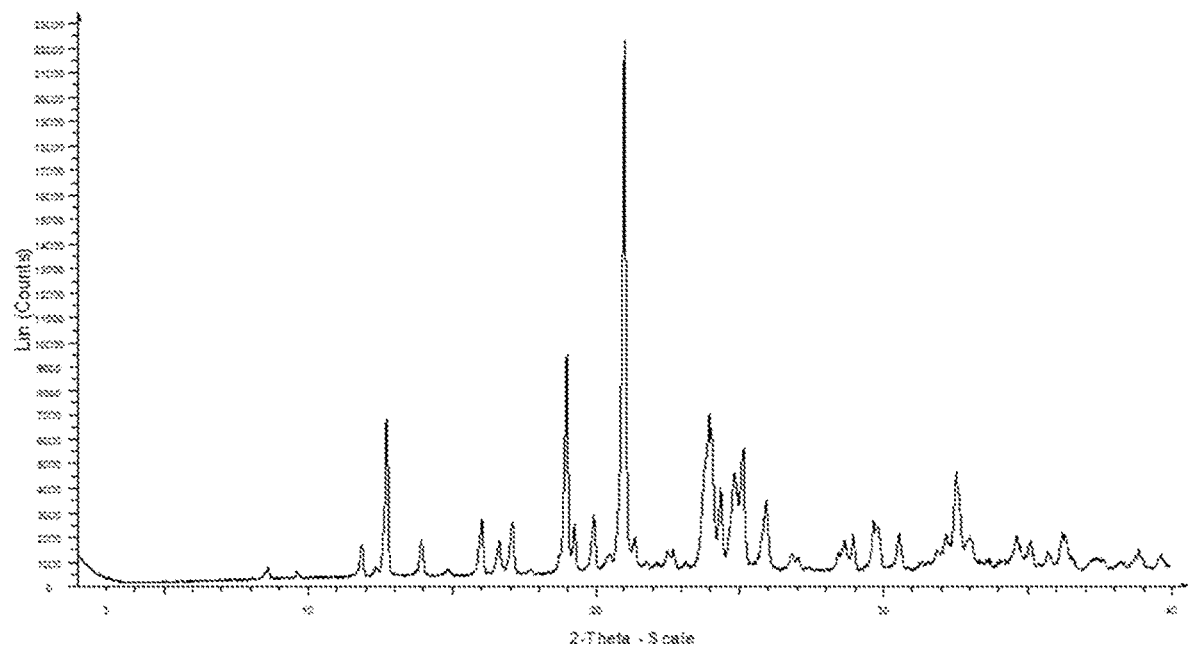
FIG. 8 depicts the XRPD pattern for crystalline form A of the hydrochloride salt of N-[4-(Chlorodifluoromethoxy)phenyl]-6-[(3R)-3-hydroxypyrrolidin-1-yl]-5-(1H-pyrazol-5-yl)pyridine-3-carboxamide according to the present invention.

In another embodiment of the present invention, crystalline form A of N-[4-(Chlorodifluoromethoxy)phenyl]-6-[(3R)-3-hydroxypyrrolidin-1-yl]-5-(1H-pyrazol-5-yl)pyridine-3-carboxamide hydrochloride is characterized by the XRPD pattern of FIGS. 8 and/or 12.

Figure 9:
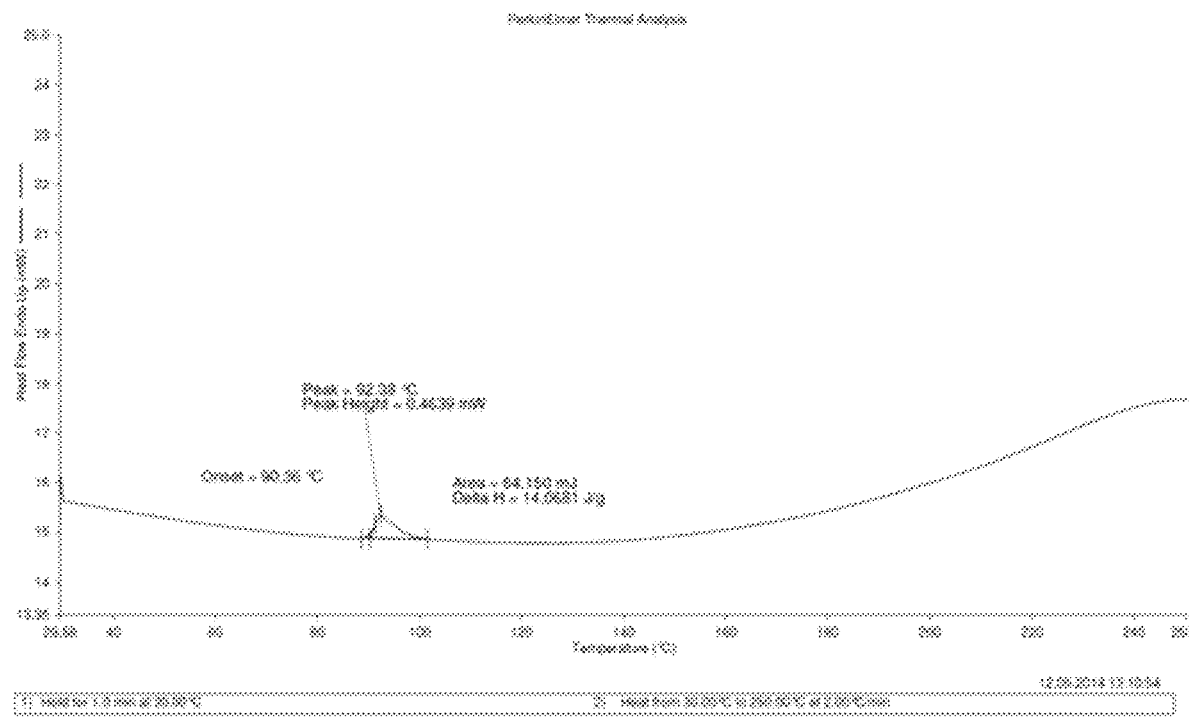
FIG. 9 depicts the differential scanning calorimetry curve for crystalline form A of the hydrochloride salt of N-[4-(Chlorodifluoromethoxy)phenyl]-6-[(3R)-3-hydroxypyrrolidin-1-yl]-5-(1H-pyrazol-5-yl)pyridine-3-carboxamide according to the present invention.
Figure 10:
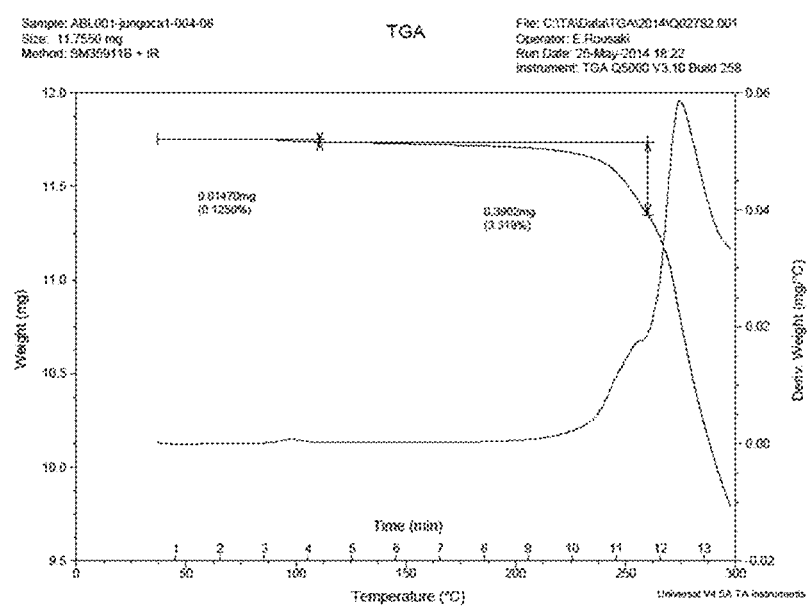
FIG. 10 depicts the thermogravimetric plot for crystalline form A of the hydrochloride salt of N-[4-(Chlorodifluoromethoxy)phenyl]-6-[(3R)-3-hydroxypyrrolidin-1-yl]-5-(1H-pyrazol-5-yl)pyridine-3-carboxamide according to the present invention.

Thermal properties of crystalline form A of N-[4-(Chlorodifluoromethoxy)phenyl]-6-[(3R)-3-hydroxypyrrolidin-1-yl]-5-(1H-pyrazol-5-yl)pyridine-3-carboxamide hydrochloride was analyzed by differential scanning calorimetry (DSC) at a scanning rate of 2° C./min. (FIG. 9) and thermogravimetric analysis (TGA) (FIG. 10).

The XRPD pattern of crystalline form B of N-[4-(Chlorodifluoromethoxy)phenyl]-6-[(3R)-3-hydroxypyrrolidin-1-yl]-5-(1H-pyrazol-5-yl)pyridine-3-carboxamide hydrochloride is characterized by at least three, or at least four, or at least five, or all, 2 theta values selected from the group consisting of 8.5°, 8.6°, 9.2°, 10.8°, 11.8°, 12.7°, 13.8°, 14.7°, 15.6°, 14.8°, 15.9°, 16.1°, 16.9°, 18.0°, 18.4°, 18.9°, 19.2°, 19.5°, 19.8°, 20.2°, 20.4°, 20.8°, 20.9°, 21.1°, 21.6°, 21.9°, 22.3°, 22.6°, 23.1°, 23.4°, 23.7°, 24.0°, 24.1°, 24.3°, 24.6°, 24.7°, 25.2°, 25.5°, 25.9°, 26.5°, 27.0°, 27.6°, 28.4°, 28.5°, 28.9°, 29.5°, and 29.8° (2θ degrees±0.2°), when measured at a temperature in the range of from 100 to 125° C. with Cu-Kalpha1,2 radiation having a wavelength of 0.1541 Å.

Figure 11:
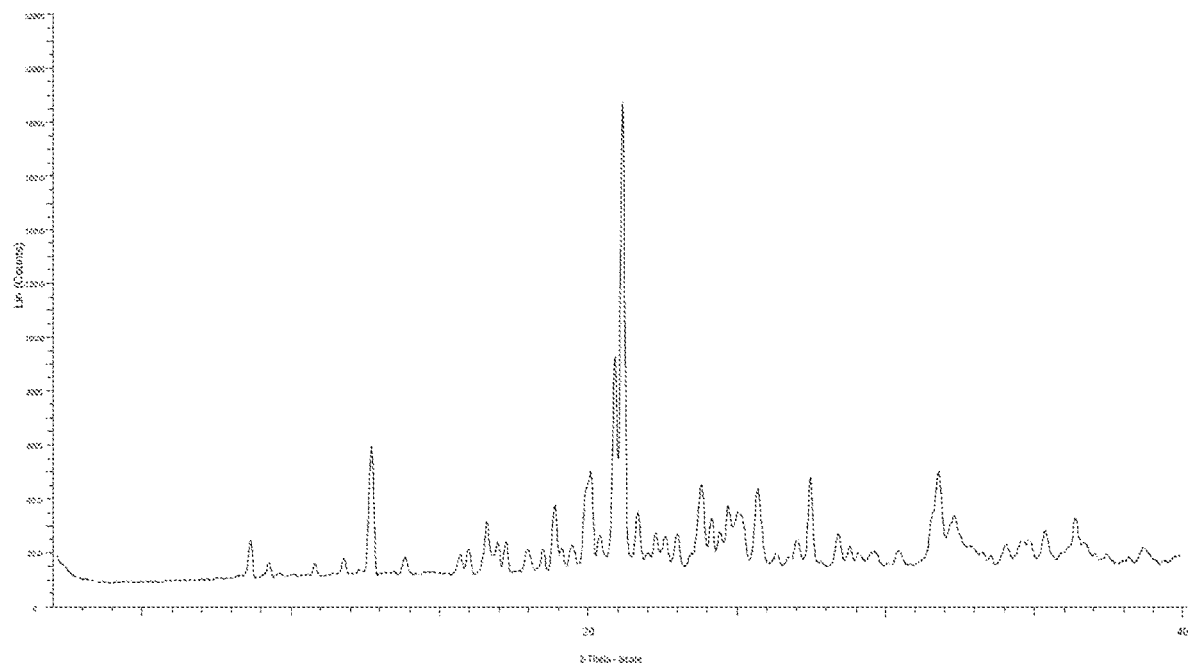
FIG. 11 depicts the XRPD pattern for crystalline form B of the hydrochloride salt of N-[4-(Chlorodifluoromethoxy)phenyl]-6-[(3R)-3-hydroxypyrrolidin-1-yl]-5-(1H-pyrazol-5-yl)pyridine-3-carboxamide according to the present invention.

In another embodiment of the present invention, crystalline form B of N-[4-(Chlorodifluoromethoxy)phenyl]-6-[(3R)-3-hydroxypyrrolidin-1-yl]-5-(1H-pyrazol-5-yl)pyridine-3-carboxamide hydrochloride is characterized by the XRPD pattern of FIGS. 11 and/or 12.

In another embodiment, the invention relates to crystalline trihydrate form $H_A$ of N-[4-(Chlorodifluoromethoxy)phenyl]-6-[(3R)-3-hydroxypyrrolidin-1-yl]-5-(1H-pyrazol- 5-yl)pyridine-3-carboxamide hydrochloride characterized by having a XRPD pattern comprising reflections at 2-Theta angles (2 theta values) of:
10.4 ±0.2°, 21.8±0.2° and 30.6±0.2°, or
10.4±0.2°, 12.0±0.2°, 16.8±0.2°, 21.8±0.2° and 30.6±0.2°, or
7.9°±0.2°, 10.4°±0.2°, 12.0°±0.2°, 13.0°±0.2°, 13.3°±0.2°, 13.8°±0.2°, 15.5°±0.2°, 15.9°±0.2°, 16.4°±0.2°, 16.8°±0.2°, 17.5°±0.2°, 19.7°±0.2°, 20.1°±0.2°, 20.5°±0.2°, 20.8°±0.2°, 21.1°±0.2°, 21.8°±0.2°, 22.2°±0.2°, 22.7°±0.2°, 23.0°±0.2°, 23.5°±0.2°, 23.9°±0.2°, 24.2°±0.2°, 24.6°±0.2°, 25.0°±0.2°, 26.0°±0.2°, 26.3°±0.2°, 26.5°±0.2°, 26.8°±0.2°, 27.8°±0.2°, 28.2°±0.2°, 28.5°±0.2°, 28.8°±0.2°, 29.5°±0.2°, 30.0°±0.2°, 30.6°±0.2°, 31.0°±0.2°, 31.3°±0.2°, 31.7°±0.2°, 32.0°±0.2°, 33.2°±0.2°, 34.0°±0.2°, 34.2°±0.2°, 35.3°±0.2°, 35.9°±0.2°, 36.7°±0.2°, 37.0°±0.2°, 37.4°±0.2°, 37.7°±0.2°, 38.2°±0.2°, 28.9°±0.2° and 39.6°±0.2°, when measured at a temperature in the range of from 20 to 25° C. with Cu-Kalpha1,2 radiation having a wavelength of 0.1541 Å.

In another embodiment, the XRPD pattern of crystalline trihydrate form $H_A$ of N-[4-(Chlorodifluoromethoxy)phenyl]-6-[(3R)-3-hydroxypyrrolidin-1-yl]-5-(1H-pyrazol-5-yl)pyridine-3-carboxamide hydrochloride is characterized by at least three, or at least four, or at least five, or all, 2 theta values selected from the group consisting of 7.9°, 10.4°, 12.0°, 13.0°, 13.3°, 13.8°, 15.5°, 15.9°, 16.4°, 16.8°, 17.5°, 19.7°, 20.1°, 20.5°, 20.8°, 21.1°, 21.8°, 22.2°, 22.7°, 23.0°, 23.5°, 23.9°, 24.2°, 24.6°, 25.0°, 26.0°, 26.3°, 26.5°, 26.8°, 27.8°, 28.2°, 28.5°, 28.8°, 29.5°, 30.0°, 30.6°, 31.0°, 31.3°, 31.7°, 32.0°, 33.2°, 34.0°, 34.2°, 35.3°, 35.9°, 36.7°, 37.0°, 37.4°, 37.7°, 38.2°, 38.9°, and 39.6° (2θ degrees±0.2°), when measured at a temperature in the range of from 20 to 25° C. with Cu-Kalpha1,2 radiation having a wavelength of 0.1541 Å.

Figure 13:
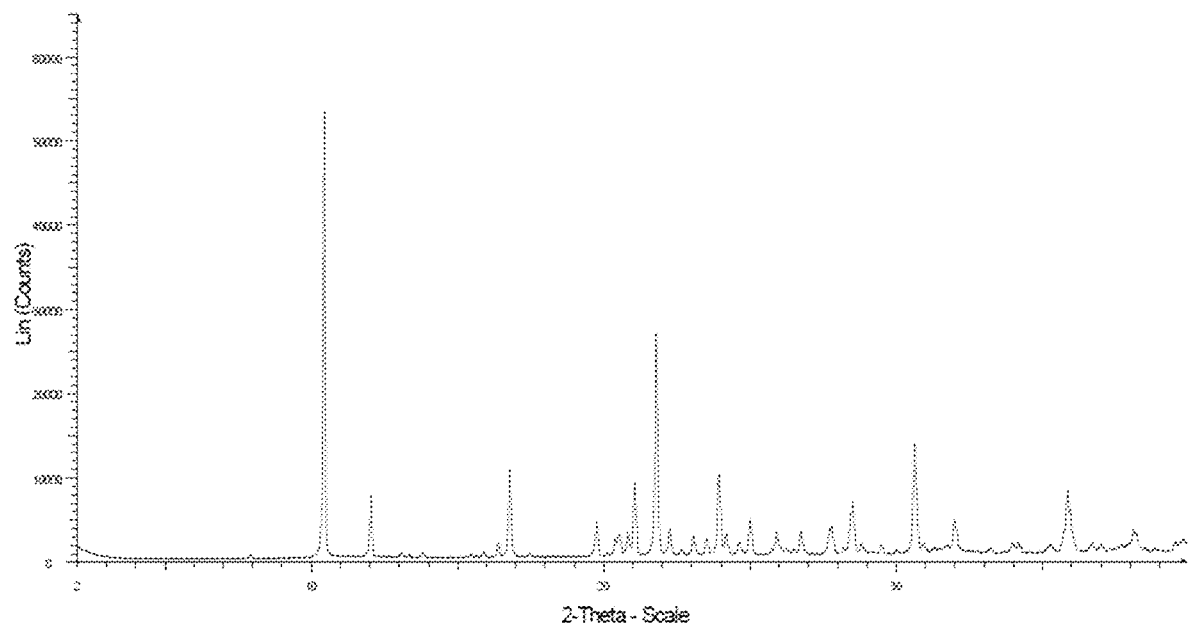
FIG. 13 depicts XRPD pattern for form HA of the hydrochloride salt of N-[4-(Chlorodifluoromethoxy)phenyl]-6-[(3R)-3-hydroxypyrrolidin-1-yl]-5-(1H-pyrazol-5-yl)pyridine-3-carboxamide according to the present invention.

In another embodiment of the present invention, crystalline trihydrate form $H_A$ of N-[4-(Chlorodifluoromethoxy)phenyl]-6-[(3R)-3-hydroxypyrrolidin-1-yl]-5-(1H-pyrazol-5-yl)pyridine-3-carboxamide hydrochloride is characterized by the XRPD pattern of FIG. 13.

Various methods can be used to achieve the crystalline forms of the free base (forms A, $S_A$, $S_B$, $S_C$, and $S_D$) and the hydrochloride salt (forms A, B, and $H_A$) of N-[4-(Chlorodifluoromethoxy)phenyl]-6-[(3R)-3-hydroxypyrrolidin-1-yl]-5-(1H-pyrazol-5-yl)pyridine-3-carboxamide. Such methods are as set forth above and as set forth in the below-presented examples and include equilibration with solvents, crystallization at room temperature, crystallization from hot saturated solutions, and precipitation by addition of solvent.

Another embodiment of the present invention is directed to a pharmaceutical composition comprising:
(a) a therapeutically effective amount of a crystalline form of N-[4-(Chlorodifluoromethoxy)phenyl]-6-[(3R)-3-hydroxypyrrolidin-1-yl]-5-(1H-pyrazol-5-yl)pyridine-3-carboxamide free base or hydrochloride salt thereof according to one of the earlier embodiments of the present invention; and
at least one pharmaceutically acceptable carrier, diluent, vehicle or excipient.

In a preferred embodiment, the crystalline form is form A of the hydrochloride salt of N-[4-(Chlorodifluoromethoxy) phenyl]-6-[(3R)-3-hydroxypyrrolidin-1-yl]-5-(1H-pyrazol-5-yl)pyridine-3-carboxamide. Preferably, more than 50%, more preferably at least 70%, still more preferably at least 80%, and most preferably at least 90%, of the crystalline form present in the composition is of one of the selected forms.

As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) nasally; (9) pulmonary; or (10) intrathecally.

The general terms used hereinbefore and hereinafter preferably have within the context of this disclosure the following meanings, unless otherwise indicated, where more general terms wherever used may, independently of each other, be replaced by more specific definitions or remain, thus defining more detailed embodiments of the invention:

The term "disintegrant" means a substance that causes the tablet to expand and dissolve when wet causing the tablet to break apart in the digestive tract, releasing the active ingredient for absorption. Disintegrants ensure that when the tablet is in contact with water, it rapidly breaks down, facilitating dissolution. Disintegrants are selected from the group consisting of crosslinked polyvinylpyrrolidone (crospovidone), crosslinked sodium carboxymethyl cellulose, for example, croscarmellose sodium and sodium starch glycolate, preferably, croscarmellose sodium.

The term "filler", also known as "diluent", means an inert ingredient often used in tablets and capsules to bulk up the content of the dosage form because the amount of active drug is too small to be handled conveniently (difficult to manufacture and handle). Examples of fillers/diluents include, but are not limited to, starch, dextrin, sucrose, sorbitol, sodium saccharin, acesulfame potassium, xylitol, aspartame, mannitol, starch, PVP (polyvinyl pyrrolidone), low molecular weight HPC (hydroxypropyl cellulose), microcrystalline cellulose (MCC), low molecular weight HPMC (hydroxypropylmethylcellulose), low molecular weight carboxymethyl cellulose, ethyl-cellulose, dicalcium phosphate, silicified microcrystalline cellulose, alginates, gelatin, polyethylene oxide, acacia, dextrin, sucrose, magnesium aluminum silicate, polymethacrylates, lactitol, lactose, suitable inorganic calcium salts, sucrose, glucose, mannitol, silicic acid, and any combination thereof. The fillers are an intra-granular component, comprising, by percentage weight, from about 60% to about 80%, based upon total weight of the tablet formulation.

The term "glidants" means a substance that is added to a powder to improve the powder's ability to "flow" or flowability. Examples include, but are not limited to, magnesium stearate, sodium stearyl fumarate, talc, magnesium carbonate, fumed silica (silicon dioxide), silica, aerosol (colloidal anhydrous/colloidal silicon dioxide) and starch, or any combination thereof.

The term "lubricants" means a compound that acts to reduce friction by interposing an intermediate layer between the tablet constituents and the die wall during compression and ejection. Examples of lubricants include, but are not limited to, stearates, sodium stearyl fumarate, magnesium salts, and magnesium stearate.

A "therapeutically effective amount" is intended to mean the amount of the inventive crystalline form that, when administered to a subject in need thereof, is sufficient to effect treatment for disease conditions alleviated by the inhibition of tyrosine kinase enzymatic activity of the Abelson protein (ABL1), the Abelson-related protein (ABL2) and related chimeric proteins, in particular BCR-ABL1. The amount of a given compound of the invention that will be therapeutically effective will vary depending upon factors such as the disease condition and the severity thereof, the identity of the subject in need thereof, etc., which amount may be routinely determined by artisans of ordinary skill in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound that produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a crystalline form of the present invention. In certain embodiments, an aforementioned formulation renders orally bioavailable an inventive crystalline form of the present invention.

Methods of preparing these formulations or compositions include the step of bringing into association an inventive crystalline form of the present invention with the carrier and, optionally, one or more accessory ingredients. In general, the formulations are prepared by uniformly and intimately bringing into association an inventive crystalline form of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution, suspension or solid dispersion in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an inventive crystalline form of the present invention as an active ingredient. An inventive crystalline form of the present invention may also be administered as a bolus, electuary or paste.

The present invention also relates to a tablet formulation comprising a crystalline form of N-[4-(Chlorodifluoromethoxy)phenyl]-6-[(3R)-3-hydroxypyrrolidin-1-yl]-5-(1H-pyrazol-5-yl)pyridine-3-carboxamide free base or hydrochloride salt, and methods of use thereof.

In one embodiment, the tablet formulation provided herein can be formulated in a unit dosage form, each dosage containing from about 5 to about 500 mg, of a crystalline form of N-[4-(Chlorodifluoromethoxy)phenyl]-6-[(3R)-3-hydroxypyrrolidin-1-yl]-5-(1H-pyrazol-5-yl)pyridine-3-carboxamide free base or hydrochloride salt.

In a further embodiment, the unit dosage form contains between 10 mg and 200 mg, of a crystalline form of N-[4-(Chlorodifluoromethoxy)phenyl]-6-[(3R)-3-hydroxypyrrolidin-1-yl]-5-(1H-pyrazol-5-yl)pyridine-3-carboxamide free base or hydrochloride salt.

In a further embodiment, the unit dosage form contains between 25 mg and 150 mg, inclusive, of a crystalline form of N-[4-(Chlorodifluoromethoxy)phenyl]-6-[(3R)-3-hydroxypyrrolidin-1-yl]-5-(1H-pyrazol-5-yl)pyridine-3-carboxamide free base or hydrochloride salt.

In a further embodiment, the unit dosage form contains 20 mg, 40 mg, or 60 mg of a crystalline form of N-[4-(Chlorodifluoromethoxy)phenyl]-6-[(3R)-3-hydroxypyrrolidin-1-yl]-5-(1H-pyrazol-5-yl)pyridine-3-carboxamide free base or hydrochloride salt.

In another embodiment, the tablet formulation of the present invention comprises, by percentage weight: 10-30% of a crystalline form of N-[4-(Chlorodifluoromethoxy)phenyl]-6-[(3R)-3-hydroxypyrrolidin-1-yl]-5-(1H-pyrazol-5-yl)pyridine-3-carboxamide free base or hydrochloride salt, 60-80% of one or more fillers, 2-10% of one or more disintegrants; and 0.2-3% of one or more glidants.

In a further embodiment, the filler is one or more selected from lactose, lactose anhydrous, lactose spray dried, directly compressible starch, hydrolyzed starch, MCC (Cellulose MK GR, Avicel PH 101), other cellulose derivatives (Natrium-CMC XL), dibasic calcium phosphate dihydrate, sorbitol, sucrose, calcium sulfate dehydrate and dextrose.

In a further embodiment, the disintegrant is one or more selected from crosslinked polyvinylpyrrolidone (crospovidone), hypromellose (low-substituted hydroxypropyl cellulose), crosslinked sodium carboxymethyl cellulose (croscarmellose sodium) and sodium starch glycolate.

In a further embodiment, the glidant is one or more selected from magnesium stearate, sodium stearyl fumarate, magnesium carbonate, fumed silica, silica, aerosol (colloidal anhydrous/colloidal silicon dioxide; Aerosil 200 PH) and starch.

In another embodiment, the tablet formulation of the present invention comprises an intra-granular phase, an extra-granular phase and a film-coating.

In a further embodiment, the intra-granular phase comprises a crystalline form of N-[4-(Chlorodifluoromethoxy)phenyl]-6-[(3R)-3-hydroxypyrrolidin-1-yl]-5-(1H-pyrazol-5-yl)pyridine-3-carboxamide free base or hydrochloride salt, lactose, Avicel PH101, HP-Celllulose low subst_40UM, Natrium-CMC XL, Aerosil 200 PH, and magnesium stearate.

In a further embodiment, the extra-granular phase comprises lactose, Cellulose MK GR, Natrium-CMC XL, Aerosil 200 PH, and magnesium stearate.

In a further embodiment, the tablet formulation of the present invention can be film-coated.

In a further embodiment, the film-coating can comprise one or more film-forming substances and can further comprise substances such as plasticizers, lubricants, colorants and/or pigments.

In a further embodiment, the film-coating comprises purified water and a mixture of one or more coating premix selected from white, yellow, red and black.

In another embodiment, the intra-granular phase contains, by percentage weight: 22% of crystalline form A of N-[4-(Chlorodifluoromethoxy)phenyl]-6-[(3R)-3-hydroxypyrrolidin-1-yl]-5-(1H-pyrazol-5-yl)pyridine-3-carboxamide hydrochloride, 33% lactose, 17% Avicel PH 101, 5% HP-Celllulose low subst 40UM, 2% Natrium-CMC XL, 0.25% Aerosil 200 PH, and 0.50% magnesium stearate.

In a further embodiment, the extra-granular phase contains, by percentage weight: 10% lactose, 6% Cellulose MK GR, 3% Natrium-CMC XL, 0.25% Aerosil 200 PH, and 1% magnesium stearate.

In a further embodiment, the film-coating contains, by percentage weight: 4.83% coating premix white; 0.16% coating premix yellow; 0.008% coating premix red and 85% purified water.

In a further embodiment, the film-coating contains, by percentage weight: 7.96% coating premix white; 0.019% coating premix red; 0.024% coating premix black and 85% purified water.

In a further embodiment, the tablet formulation comprises an intra-granular phase, an extra-granular phase and a film-coating wherein: said intra-granular phase comprises the crystalline form A of N-[4-(Chlorodifluoromethoxy)phenyl]-6-[(3R)-3-hydroxypyrrolidin-1-yl]-5-(1H-pyrazol-5-yl)pyridine-3-carboxamide hydrochloride, lactose, Avicel PH101, HP-Celllulose low subst 40UM, Natrium-CMC XL, Aerosil 200 PH, and magnesium stearate; said extra-granular phase comprises lactose, Cellulose MK GR, Natrium-CMC XL, Aerosil 200 PH, and magnesium stearate; and said film-coating can comprise one or more film-forming substances and can further comprise substances such as plasticizers, intestinal lubricants, colorants and/or pigments.

In a further embodiment, the tablet formulation comprises an intra-granular phase, an extra-granular phase and a film-coating wherein: said intra-granular phase comprises, by percentage weight: about 22% of crystalline form A of N-[4-(Chlorodifluoromethoxy)phenyl]-6-[(3R)-3-hydroxypyrrolidin-1-yl]-5-(1H-pyrazol-5-yl)pyridine-3-carboxamide hydrochloride, about 33% lactose, about 17% Avicel PH 101, about 5% HP-Celllulose low subst 40UM, about 2% Natrium-CMC XL, about 0.25% Aerosil 200 PH, and about 0.50% magnesium stearate.

In a further embodiment, the extra-granular phase contains, by percentage weight: about 10% lactose, about 6% Cellulose MK GR, about 3% Natrium-CMC XL, about 0.25% Aerosil 200 PH, about 1% magnesium stearate; and the film-coating contains, by percentage weight:

about 4.83% coating premix white; about 0.16% coating premix yellow; about 0.008% coating premix red and about 85% purified water.

In another embodiment, the extra-granular phase contains, by percentage weight: about 10% lactose, about 6% Cellulose MK GR, about 3% Natrium-CMC XL, about 0.25% Aerosil 200 PH, about 1% magnesium stearate; and the film-coating contains, by percentage weight: about 7.96% coating premix white; about 0.019% coating premix red; about 0.024% coating premix black and about 85% purified water.

The present invention also relates to a process for the production of a tablet comprising a crystalline form of N-[4-(Chlorodifluoromethoxy)phenyl]-6-[(3R)-3-hydroxypyrrolidin-1-yl]-5-(1H-pyrazol-5-yl)pyridine-3-carboxamide free base or hydrochloride salt, wherein the process comprises:

(a) blending the intra-granular phase ingredients: crystalline form A of N-[4-(Chlorodifluoromethoxy)phenyl]-6-[(3R)-3-hydroxypyrrolidin-1-yl]-5-(1H-pyrazol-5-yl)pyridine-3-carboxamide hydrochloride, Avicel PH101, HP-Celllulose low subst 40UM, Natrium-CMC XL, Aerosil 200 PH and magnesium stearate;

(b) sieving, blending, roller compacting and milling the blended ingredients from step (a);

(c) blending the extra-granular phase ingredients: lactose, Cellulose MK GR, Natrium-CMC XL, Aerosil 200 PH and magnesium stearate;

(d) sieving the ingredients from step (c);

(e) blending the ingredients from step (b) and step (d);

(f) compressing the ingredients of step (e) into tablets and dedusting said tablets;

(g) forming a suspension of the film-coating: comprises purified water and a mixture of one or more coating premix selected from white, yellow, red and black; and (h) film-coating the dedusted tablets of (f).

Another aspect of the present invention is directed to a method of treating an ABL1/BCR-ABL1-mediated disorder comprising the step of administering to a subject in need of such treatment a therapeutically effective amount of a crystalline form of N-[4-(Chlorodifluoromethoxy)phenyl]-6-[(3R)-3-hydroxypyrrolidin-1-yl]-5-(1H-pyrazol-5-yl)pyridine-3-carboxamide free base or hydrochloride salt thereof according to one of the earlier embodiments of the present invention. In a preferred embodiment, the crystalline form is form A of the hydrochloride salt of N-[4-(Chlorodifluoromethoxy)phenyl]-6-[(3R)-3-hydroxypyrrolidin-1-yl]-5-(1H-pyrazol-5-yl)pyridine-3-carboxamide. Preferably, more than 50%, more preferably at least 70%, still more preferably at least 80%, and most preferably at least 90%, of the crystalline form administered is of one of the inventive forms. As noted above, illustrative modes of administration include oral, nasal, parenteral, topical, transdermal, and rectal. Administration of the crystalline form may be accomplished by administration of a pharmaceutical composition of this invention or via any other effective means.

Specific embodiments of the invention will now be demonstrated by reference to the following examples. It should be understood that these examples are disclosed solely by way of illustrating the invention and should not be taken in any way to limit the scope of the present invention.

EXAMPLES

General Test Conditions

The following procedures were employed under each test condition.

Equilibration With Solvent at 25° C.

For equilibration at 25° C., about 50 mg of the drug substance was equilibrated with 1 ml solvent for at least 1 week and about 4 weeks in Eppendorf shaker at 25° C. ±0.5. The solutions were filtered and dried for 10 minutes in the air. The solid part was investigated by XRPD (X-ray powder diffraction). If the information from XRPD was insufficient to evaluate the change, additional investigations by TG and NMR were performed.

Equilibration With Solvent at 50° C.

For equilibration with solvent at 50° C., about 50 mg of drug substance was equilibrated with 1 ml solvent for 2 days in in Eppendorf shaker at 50° C. ±0.1. The filtrate was investigated as noted above.

Crystallization at 25° C.

Combined with equilibrations, if solubility determined by gravimetry, the residue was examined for its polymorphic form.

Crystallization From Hot Saturated Solutions

For crystallization from hot saturated solutions, approximately 300 mg of drug substance was dissolved in the minimal amount of solvent at 60° C. and hot filtrated. No remaining crystals were visible. The solutions were put in an ice bath and agitated. The precipitates were collected on a filter, dried and investigated as described in the equilibration example.

Precipitation by Addition of Solvent

For precipitation by addition of solvent, the drug substance was dissolved in a solvent where the solubility is high and a solvent in which the substance is highly insoluble was added. The precipitate was treated as described in the equilibration example.

X-Ray Diffraction

The X-ray powder diffraction (XRPD) patterns described herein were recorded on a Bruker D8 Advance diffractometer using CuKa radiation. The XRPD pattern was recorded between 2° and 40° (2-theta).

One of ordinary skill in the art will appreciate that an XRPD pattern may be obtained with a measurement error that is dependent upon the measurement conditions employed. In particular, it is generally known that intensities in an XRPD pattern may fluctuate depending upon measurement conditions employed. It should be further understood that relative intensities may also vary depending upon experimental conditions and wavelength of X-ray radiation used. The agreement in the 2-theta-diffraction angles between specimen and reference is within 0.2° for the same crystal form and such degree of measurement error should be taken into account as pertaining to the aforementioned diffraction angles. Consequently, it is to be understood that the crystal forms of the instant invention are not limited to the crystal forms that provide X-ray diffraction patterns completely identical to the XRPD patterns depicted in the accompanying Figures disclosed herein. Any crystal forms that provide XRPD patterns substantially identical to those disclosed in the accompanying Figures fall within the scope of the present invention. The ability to ascertain substantial identities of XRPD patterns is within the purview of one of ordinary skill in the art.

Thermogravimetric Method

The TGA instruments used to test the crystalline forms was a TA Q5000. Samples of 10 to 20 milligrams were analyzed at a heating rate of 20° C. per minute in the temperature range between 30° C. and about 300° C.

Differential Scanning Calorimetry (DSC)

The DSC instrument used to test the crystalline forms was a Mettler DSC1 or a Perkin Elmer Diamond. The instrument was programmed to heat at 10° C. per minute in the temperature range between 30° C. and 300° C. under nitrogen flow at 30 mL/min.

Example 1

Preparation of Form A of N-[4-(Chlorodifluoromethoxy)phenyl]-6-[(3R)-3-hydroxypyrrolidin-1-yl]-5-(1H-pyrazol-5-yl)pyridine-3-carboxamide Free Base N-[4-(Chlorodifluoromethoxy)phenyl]-6-[(3R)-3-hydroxypyrrolidin-1-yl]-5-(1H-pyrazol-5-yl)pyridine-3-carboxamide, the starting marterial, is prepared in accordance to Example 9 of WO 2013/171639 A1. The starting material is suspended in methanol and heated at 30° C. to obtain a solution. Water is added to crystallize the free base. The suspension is cooled to 10° C. and crystal form A of the free base is isolated by filtration and drying.

The XRPD pattern for crystal form A of the free base is shown in FIG. 1. The differential scanning calorimetry curve of form A of the free base showed an onset of melting at about 194° C. followed by a peak at about 198° C. as shown in FIG. 2. FIG. 3 depicts the thermogravimetric plot for crystal form A of the free base. The single crystal data for crystal form A of the free base at 100K is as follows:

| | |
|---|---|
| Molecular formula: | $C_{20}H_{18}ClF_2N_5O_3$ |
| Molecular weight: | 449.84 |
| Space symmetry | monoclinic |
| Space group | C2 |
| Cell Volume (Å$^3$) | 2001.0(8) |
| Crystal Density (g/cm$^3$) | 1.493 |
| a (Å) | 14.422(3) |

| | |
|---|---|
| b (Å) | 9.368(2) |
| c (Å) | 14.989(4) |
| beta (°) | 98.853(12) |
| z | 4 |

Example 2

Figure 4:
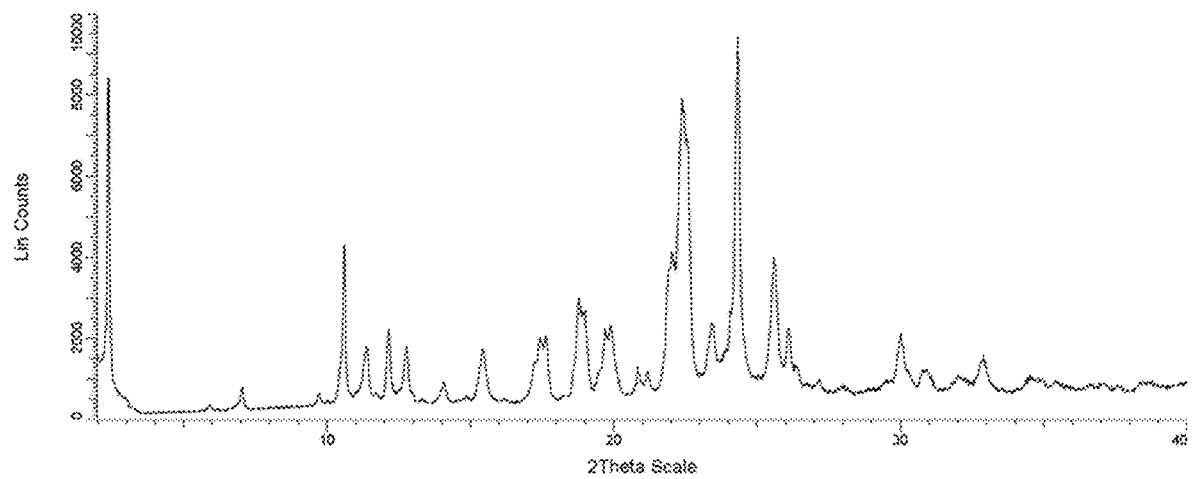
FIG. 4 depicts the XRPD pattern for form $S_A$ of N-[4-(Chlorodifluoromethoxy)phenyl]-6-[(3R)-3-hydroxypyrrolidin-1-yl]-5-(1H-pyrazol-5-yl)pyridine-3-carboxamide free base according to the present invention.

Preparation of Form SA of N-[4-(Chlorodifluoromethoxy)phenyl]-6-[(3R)-3-hydroxypyrrolidin-1-yl]-5-(1H-pyrazol-5-yl)pyridine-3-carboxamide Free Base Methanol solvate form SA of the free base was obtained by equilibration of crystal form A of the free base in methanol at 50° C. and crystallization from hot saturated solutions of crystal form A of the free base in methanol at 60° C. The XRPD pattern for crystal form SA of the free base is shown in FIG. 4.

Example 3

Figure 5:
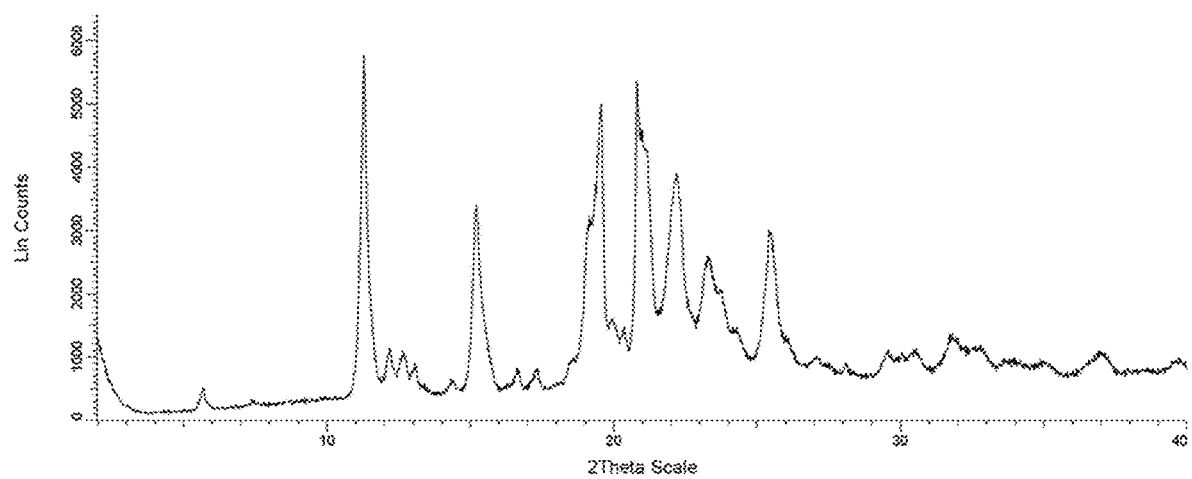
FIG. 5 depicts the XRPD pattern for form $S_B$ of N-[4-(Chlorodifluoromethoxy)phenyl]-6-[(3R)-3-hydroxypyrrolidin-1-yl]-5-(1H-pyrazol-5-yl)pyridine-3-carboxamide free base according to the present invention.

Preparation of Form $S_B$ of N-[4-(Chlorodifluoromethoxy)phenyl]-6-[(3R)-3-hydroxypyrrolidin-1-yl]-5-(1H-pyrazol-5-yl)pyridine-3-carboxamide Free Base 1-propanol solvate form $S_B$ of the free base was obtained by equilibration of crystal form A of the free base in 1-propanol at 25° C. (for 1 and 4 weeks) and at 50° C. as well as crystallization at 25° C. and hot saturated solutions at 60° C. in 1-propanol. The XRPD pattern for crystal form $S_B$ of the free base is shown in FIG. 5.

Example 4

Figure 6:
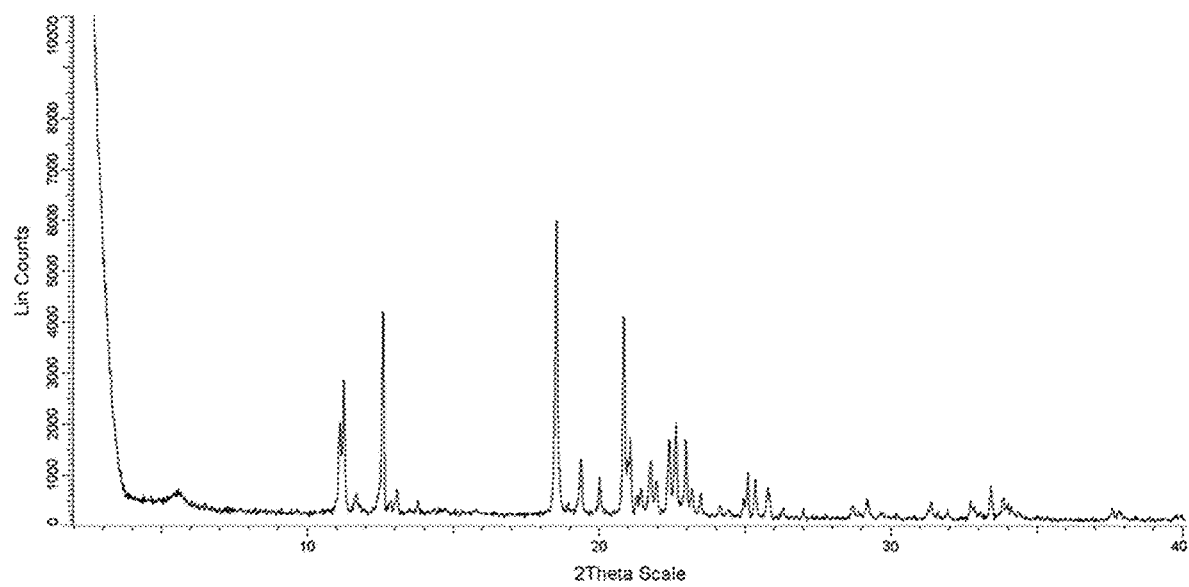
FIG. 6 depicts the XRPD pattern for form $S_C$ of N-[4-(Chlorodifluoromethoxy)phenyl]-6-[(3R)-3-hydroxypyrrolidin-1-yl]-5-(1H-pyrazol-5-yl)pyridine-3-carboxamide free base according to the present invention.

Preparation of Form $S_C$ of N-[4-(Chlorodifluoromethoxy)phenyl]-6-[(3R)-3-hydroxypyrrolidin-1-yl]-5-(1H-pyrazol-5-yl)pyridine-3-carboxamide Free Base Ethanol solvate form $S_C$ of the free base was obtained by equilibration of crystal form A of the free base in ethanol at 50° C. and crystallization from hot saturated solutions at 60° C. in ethanol. The XRPD pattern for crystal form Sc of the free base is shown in FIG. 6.

Example 5

Figure 7:
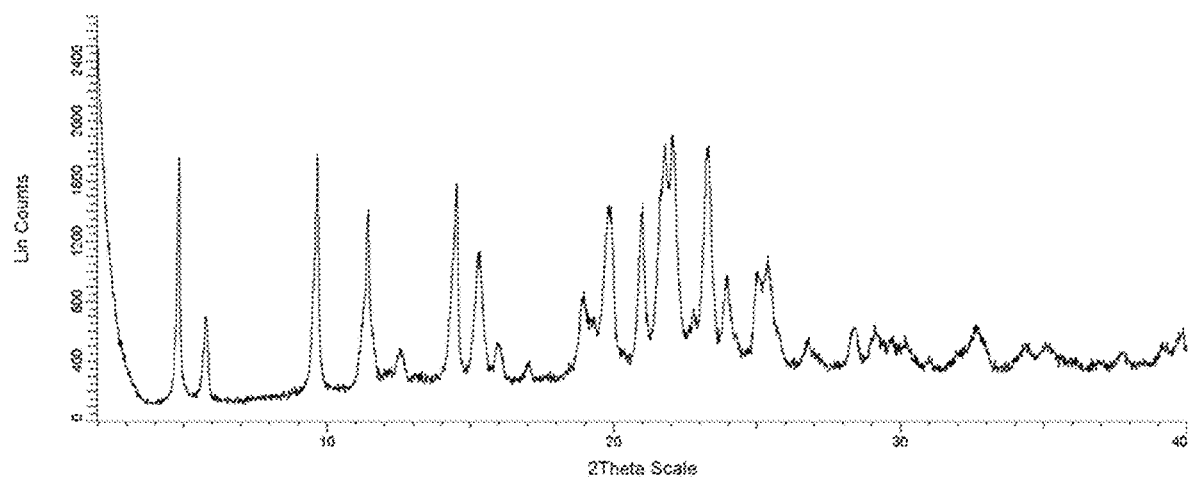
FIG. 7 depicts the XRPD pattern for form $S_D$ of N-[4-(Chlorodifluoromethoxy)phenyl]-6-[(3R)-3-hydroxypyrrolidin-1-yl]-5-(1H-pyrazol-5-yl)pyridine-3-carboxamide free base according to the present invention.

Preparation of Form $S_D$ of N-[4-(Chlorodifluoromethoxy)phenyl]-6-[(3R)-3-hydroxypyrrolidin-1-yl]-5-(1H-pyrazol-5-yl)pyridine-3-carboxamide Free Base Acetone solvate form $S_D$ of the free base was obtained by precipitation by addition of solvent of crystal form A of the free base in acetone and water. The XRPD pattern for crystal form $S_D$ of the free base is shown in FIG. 7.

Example 6

Preparation of Form A of N-[4-(Chlorodifluoromethoxy)phenyl]-6-[(3R)-3-hydroxypyrrolidin-1-yl]-5-(1H-pyrazol-5-yl)pyridine-3-carboxamide hydrochloride Crystal form A of N-[4-(Chlorodifluoromethoxy)phenyl]-6-[(3R)-3-hydroxypyrrolidin-1-yl]-5-(1H-pyrazol-5-yl) pyridine-3-carboxamide free base is suspended in methanol and hydrochloric acid is added. The suspension is heated to obtain a solution. Tert-butyl methyl ether (TBME) is added to form crystal form A of the hydrochloride salt. The suspension is cooled and crystal form A of the hydrochloride salt is isolated by filtration and drying.

Alternatively, crystal form A of the hydrochloride salt may also be isolated under the following conditions:

N-[4-(Chlorodifluoromethoxy)phenyl]-6-[(3R)-3-hydroxypyrrolidin-1-yl]-5-(1H-pyrazol-5-yl)pyridine-3-carboxamide (1 wt) is dissolved in methanol (8 wt) at 35° C. Hydrochloride acid (1.15 eq) is added to the solution to form crystal form A of the hydrochloride salt. The solution is heated to 50° C. Tert-butyl methyl ether (TBME) (5 wt) is added over 35 minutes. The solution is seeded with seeds of crystal form A of the hydrochloride salt (0.0009 wt) slurried in TBME (0.01 vol). The suspension is aged for 135 minutes. TBME (9.25 wt) is added over 1.5 hour. The slurry is cooled to IT=0° C. over 3 hours and held at 0° C. Afterwards the slurry is filtered and the cake is washed with methanol:TBME 1:9w/w (2V) and then with TBME (2V). The wet cake is dried under vacuum at 50° C. for 24 hours.

The XRPD pattern for crystal form A of the hydrochloride salt is shown in FIG. 8. The differential scanning calorimetry curve of form A of the hydrochloride salt depicts an endothermic event at about 90° C. as shown in FIG. 9. FIG. 10 depicts the thermogravimetric plot for crystal form A of the hydrochloride salt. The single crystal data for crystal form A of the hydrochloride salt at 100K is as follows:

| | |
|---|---|
| Space symmetry | Triclinic |
| Space group | P1 |
| Cell Volume (Å³) | 1053.6(6) |
| Crystal Density (g/cm³) | 1.533 |
| a (Å) | 8.203(3) |
| b (Å) | 11.116(3) |
| c (Å) | 12.627(4) |
| beta (°) | 97.711(12) |
| Z | 2 |

The single crystal data for crystal form A of the hydrochloride salt at 298K is as follows:

| | |
|---|---|
| Space symmetry | Triclinic |
| Space group | P1 |
| Cell Volume (Å³) | 1082.9(6) |
| Crystal Density (g/cm³) | 1.491 |
| a (Å) | 8.245(3) |
| b (Å) | 11.352(4) |
| c (Å) | 12.697(4) |
| beta (°) | 97.289(18) |
| Z | 2 |

Example 7

Preparation of Form A of N-[4-(Chlorodifluoromethoxy)phenyl]-6-[(3R)-3-hydroxypyrrolidin-1-yl]-5-(1H-pyrazol-5-yl)pyridine-3-carboxamide hydrochloride Seed Crystals Crystal form A of N-[4-(Chlorodifluoromethoxy)phenyl]-6-[(3R)-3-hydroxypyrrolidin-1-yl]-5-(1H-pyrazol-5-yl) pyridine-3-carboxamide free base and hydrochloric acid are dissolved in isopropanol and heated until complete dissolution of the solids. The clear solution is allowed to equilibrate at RT and spontaneous crystallization in observed. The solid material is isolated, dried and analyzed by XRPD, NMR and HPLC.

Example 8

Preparation of Form B of N-[4-(Chlorodifluoromethoxy)phenyl]-6-[(3R)-3-hydroxypyrrolidin-1-yl]-5-(1H-pyrazol-5-yl)pyridine-3-carboxamide hydrochloride Crystal forms A and B of the hydrochloride salt are enantiotropically related. Upon heating, crystal Form A of N-[4-(Chlorodifluoromethoxy)phenyl]-6-[(3R)-3-hydroxypyrrolidin-1-yl]-5-(1H-pyrazol-5-yl)pyridine-3-carboxamide hydrochloride spontaneously converts into Form B. The phenomenon is fully reversible, providing that no decomposition occurred (decomposition observed above 240° C.). Form B spontaneously transforms back into Form A at ambient conditions. While the transition temperature could not be determined accurately, a range from 65° C. to 90° C. has been defined. Crystal form A of the hydrochloride salt is the thermodynamically stable form below this transition temperature and crystal form B is the favored form above it.

Figure 12:
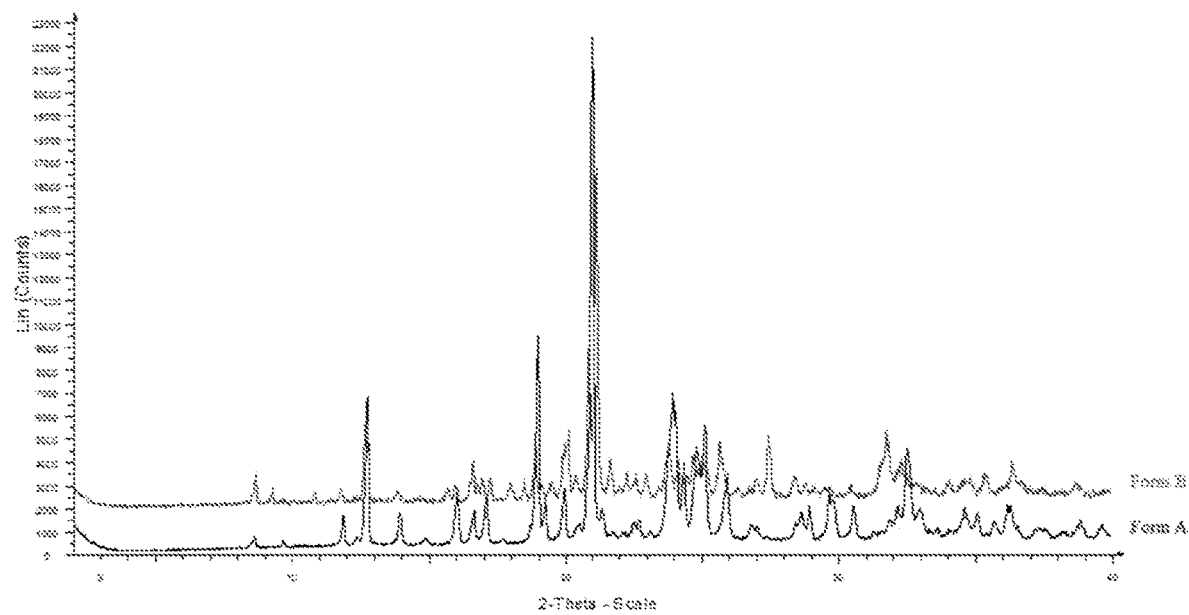
FIG. 12 depicts XRPD patterns for forms A and B of the hydrochloride salt of N-[4-(Chlorodifluoromethoxy)phenyl]-6-[(3R)-3-hydroxypyrrolidin-1-yl]-5-(1H-pyrazol-5-yl)pyridine-3-carboxamide according to the present invention.

The XRPD pattern for crystal form B of the hydrochloride salt is shown in FIG. 11. A superposition of XRPD patterns of crystal forms A and B of the hydrochloride salt is shown in FIG. 12. The single crystal data for crystal form B of the hydrochloride salt at 363K is as follows:

| Space symmetry | Triclinic |
| --- | --- |
| Space group | P1 |
| Cell Volume (Å$^3$) | 1114.6(15) |
| Crystal Density (g/cm$^3$) | 1.449 |
| a (Å) | 9.957(8) |
| b (Å) | 10.461(8) |
| c (Å) | 11.146(8) |
| beta (°) | 75.71(5) |
| Z | 2 |

Example 9

Thermodynamic Stability of Forms A and B of N-[4-(Chlorodifluoromethoxy)phenyl]-6-[(3R)-3-hydroxypyrrolidin-1-yl]-5-(1H-pyrazol-5-yl)pyridine-3-carboxamide hydrochloride During thermal investigation, no melting point for either crystal forms A and B of the hydrochloride salt could be determined because form B was found to decompose prior to melting when heated up to 300° C.

The impact of the heating rate on transition temperature was evaluated by heating and cooling cycles at different rates of 40, 20, 10, 5, 1 and 0.5° C. per minute from -20° C. to 200° C. and then back to -20° C. Hermetically sealed, closed gold crucibles were used for all of these measurements.

For each experiment (different heating rate), a fresh sample was prepared. The observed transition temperatures are listed in Table 3.

TABLE 3

| Transition Temperatures | | | |
| --- | --- | --- | --- |
| heating/cooling rate | sample weight [mg] | transition A → B | transition B → A |
| 40° C./min | 3.077 | 103.7° C. | 32.2° C. |
| 20° C./min | 3.396 | 104.8° C. | 34.7° C. |
| 10° C./min | 3.400 | 102.1° C. | 37.5° C. |
| 5° C./min | 7.005 | 100.3° C. | 38.5° C. |
| 1° C./min | 8.994 | 96.5° C. | 53.8° C. |
| 0.5° C./min | 8.331 | 95.1° C. | 60.5° C. |

Forms A and B are identified and confirmed by its corresponding XRPD pattern and thermal parameters.

Example 10

Preparation of Form H$_A$ of N-[4-(Chlorodifluoromethoxy)phenyl]-6-[(3R)-3-hydroxypyrrolidin-1-yl]-5-(1H-pyrazol-5-yl)pyridine-3-carboxamide hydrochloride When equilibrated in water, depending on pH, crystal form A of the hydrochloride salt, is either prone to disproportionate (pH>3.5) and recrystallize out as crystal form A of the free base, remain stable, or is converting into the trihydrate H$_A$ (pH 1). The XRPD pattern for crystal form H$_A$ of the free base is shown in FIG. 13.

Example 11

Tablet Formulation Comprising Crystalline Form A of N-[4-(Chlorodifluoromethoxy)phenyl]-6-[(3R)-3-hydroxypyrrolidin-1-yl]-5-(1H-pyrazol-5-yl)pyridine-3-carboxamide hydrochloride A number of trials were undertaken to develop a suitable formulation of N-[4-(Chlorodifluoromethoxy)phenyl]-6-[(3R)-3-hydroxypyrrolidin-1-yl]-5-(1H-pyrazol-5-yl)pyridine-3-carboxamide that allows for reasonable dose strength with immediate release properties and acceptable size, favorable dissolution profile, and economical manufacturing process. Crystal form A of N-[4-(Chlorodifluoromethoxy)phenyl]-6-[(3R)-3-hydroxypyrrolidin-1-yl]-5-(1H-pyrazol-5-yl)pyridine-3-carboxamide hydrochloride film coated tablets was discovered to exhibit advantageous pharmacological properties for drug development.

| | 20 mg and 40 mg Tablet Formulation | | |
| --- | --- | --- | --- |
| | Component | Composition (%) | 20 mg API Composition per unit (mg/unit) | 40 mg API Composition per unit (mg/unit) |
| Internal Phase | Compound 1[1,2] | 21.62 | 21.62 | 43.24 |
| | Lactose[2] | 32.91 | 32.91 | 65.82 |
| | Avicel PH 101[2] | 17.72 | 17.72 | 35.44 |
| | HP-Cellulose Low Subst_40UM.001 | 5.00 | 5.00 | 10.00 |
| | Natrium-CMC XL | 2.00 | 2.00 | 4.00 |
| | Aerosil 200PH | 0.25 | 0.25 | 0.50 |
| | Magnesium Stearate | 0.50 | 0.50 | 1.00 |

-continued

| | 20 mg and 40 mg Tablet Formulation | | |
|---|---|---|---|
| | Component | Composition (%) | 20 mg API Composition per unit (mg/unit) | 40 mg API Composition per unit (mg/unit) |
|---|---|---|---|---|
| External Phase | Lactose | 10.20 | 10.20 | 20.40 |
| | Cellulose MK GR | 5.55 | 5.55 | 11.10 |
| | Natrium-CMC XL | 3.00 | 3.00 | 6.00 |
| | Aerosil 200PH | 0.25 | 0.25 | 0.50 |
| | Magnesium stearate | 1.00 | 1.00 | 2.00 |
| Total Core Tablet | | 100.00 | 100.00 | 200.00 |
| | Coating Premix White FMP | | 4.832 | 7.957 |
| | Coating Premix Yellow FMP | | 0.160 | |
| | Coating Premix Red FMP | | 0.008 | 0.019 |
| | Coating Premix Black FMP | | | 0.024 |
| | Water purified[3] | | | |
| Total with Coating | | | 105.0 | 208.0 |

[1] Compound 1 is active product ingredient (API) crystal form A of N-[4-(Chlorodifluoromethoxy)phenyl]-6-[(3R)-3-hydroxypyrrolidin-1-yl]-5-(1H-pyrazol-5-yl)pyridine-3-carboxamide hydrochloride.
[2] Excess quantity is taken to compensate any drug substance potency below 100%.
[3] Removed during processing.

Example 12

Manufacturing Process for Film Coated Tablets Comprising Crystal Form A of N-[4-(Chlorodifluoromethoxy)phenyl]-6-[(3R)-3-hydroxypyrrolidin-1-yl]-5-(1H-pyrazol-5-yl)pyridine-3-carboxamide hydrochloride The process described below may be reasonably adjusted, while maintaining the same basic production steps, to compensate for different batch sizes and/or equipment characteristics, and/or on the basis of experience:

The core tablet manufacture consists of standard mixing, sieving, dry granulation, tableting and film coating steps. The procedure is as follows:

Step 1: All components of the internal phase were mixed in the following order: lactose, Compound 1, Natrium-CMC XL, Aerosil 200 PH, HP-Celllulose low subst_40UM and Avicel PH101 into a suitable container. The mixture was blended in a diffusion mixer.

Step 2: The blend from step 1 was screened using a screening mill fitted with 0.800 mm hand sieve or oscillating mill. The mixture was further blended in a diffusion mixer with magnesium stearate.

Step 3: The blend from step 2 is compacted using a roller compactor and milled using a screening mill fitted with 0.8 mm screen.

Step 4: The external phase excipients were loaded into a suitable blending bin in the following order: Lactose, Natrium-CMC XL, Aerosil 200 PH and Cellulose MK GR after being screened using a screening mill fitted with 0.800 mm hand sieve or oscillating mill. The mixture was blended with the blend from Step 3 in a diffusion mixer.

Step 5: The mixture from blend from step 4 was further blended in a diffusion mixer with magnesium stearate.

Step 6: The mixture from step 5 was compressed into tablets using a rotary tableting machine. The core tablets were dedusted and checked form metal.

Step 7: Coating premixes and purified water were mixed to form a coating suspension that was used to film-coat the dedusted tablets of step 6 in a perforated pan coater.

Figure 14:
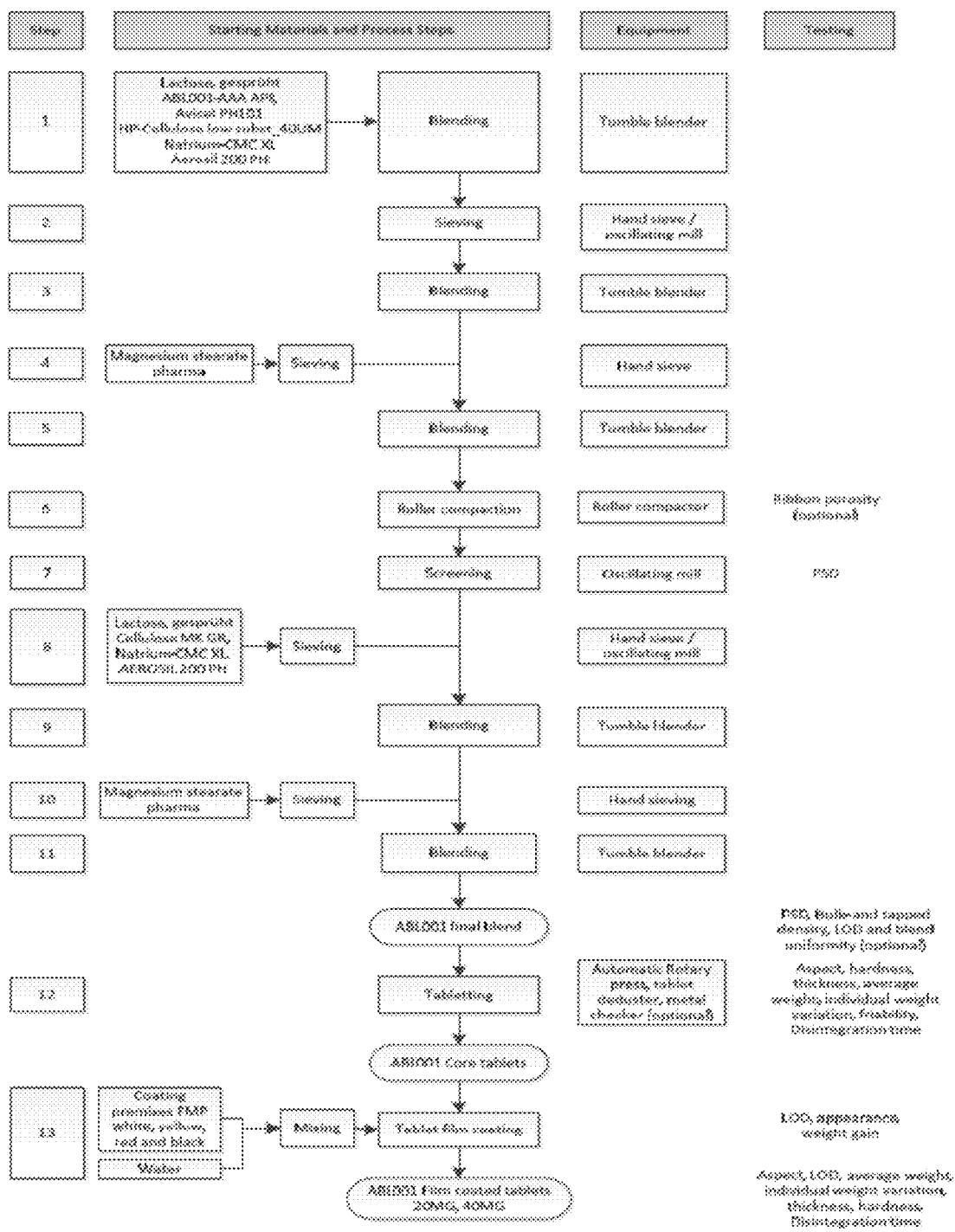
FIG. 14 depicts a flow diagram of the manufacturing process used for the manufacture of tablets comprising crystalline form A of N-[4-(Chlorodifluoromethoxy)phenyl]-6-[(3R)-3-hydroxypyrrolidin-1-yl]-5-(1H-pyrazol-5-yl)pyridine-3-carboxamide hydrochloride.

An illustration of this process is found in FIG. 14.

Example 13

Pharmacokinetic Study

A dog study was conducted with capsule formulations of a solid amorphous dispersion of N-[4-(Chlorodifluoromethoxy)phenyl]-6-[(3R)-3-hydroxypyrrolidin-1-yl]-5-(1H-pyrazol-5-yl)pyridine-3-carboxamide and of crystalline form A of N-[4-(Chlorodifluoromethoxy)phenyl]-6-[(3R)-3-hydroxypyrrolidin-1-yl]-5-(1H-pyrazol-5-yl)pyridine-3-carboxamide to demonstrate the food effect prediction in humans. The mean ±SD pharmacokinetic parameters of the solid dispersion formulation and the crystalline formulation were evaluated in plasma of dog model (n=3) per group following oral administration of 150 mg dose, fasted overnight before the dose and for 2 hours post-dose, under fast and fed state to observe fed impact on absorption. Serial blood samples were collected from each animal pre-dose and at 0.25, 0.5, 1, 2, 4, 8, 24, 30, and 48 h post-dose.

TABLE 4

Study Summary and mean ± SD pharmacokinetic parameters

| Formulation/ Treatment | Solid dispersion formulation w/o meal | Solid dispersion formulation w/ meal | Crystalline formulation w/o meal | Crystalline formulation w/ meal |
|---|---|---|---|---|
| Tmax (h) * | 2.0 (2.0-2.0) | 3.3 (2.0-4.0) | 2.0 (1.0-4.0) | 3.3 (2.0-4.0) |
| Cmax (ng/mL) | 5600 ± 2520 | 3880 ± 764 | 2900 ± 1690 | 3080 ± 857 |
| Apparent T1/2 (h) | 3.29 ± 0.135 | 3.68 ± 0.163 | 3.25 ± 0.115 | 3.4 ± 0.0791 |
| AUC0-48 h (ng · h/mL) | 41300 ± 18200 | 32000 ± 7920 | 10300 ± 1520 | 26000 ± 8450 |
| AUCinf (ng · h/mL) | 41400 ± 18200 | 32100 ± 7930 | 11200 ± 2990 | 26100 ± 8600 |

* Tmax given as mean and range

The food effect is formulation dependent. The following observations were made:

1. For the crystalline formulation, there was 133% (AUCinf, 26100 vs 11200 ng·h/mL) increase of exposure after dosing with meal compared with that without a meal (positive food effect).

2. For the solid dispersion formulation, there was 22.5% (AUCinf, 41400 vs 32100 ng·h/mL) decrease of exposure after dosing with a meal compared with that without a meal (negative food effect).

3. Under fasting conditions, there was a 3.7-fold higher exposure (AUCinf, 41400 vs 11200 ng·h/mL) with the solid dispersion formulation as compared to the crystalline formulation.

Example 14

Pharmacokinetic Study

A dog study was conducted with a formulation of crystalline form A of N-[4-(Chlorodifluoromethoxy)phenyl]-6-[(3R)-3-hydroxypyrrolidin-1-yl]-5-(1H-pyrazol-5-yl)pyridine-3-carboxamide hydrochloride to demonstrate the food effect prediction in humans.

The mean±SD pharmacokinetic parameters of the formulation was evaluated in plasma of dog model (n=3) following oral administration of 150 mg, fasted for approximately 18 hours, and fed 2 hours after dosing, to observe fed impact on absorption. Serial blood samples were collected from each animal pre-dose and at 0.25, 0.5, 1, 2, 4, 8, 24, 30, and 48 h post-dose.

TABLE 5

Study Summary and mean ± SD pharmacokinetic parameters

| Formulation/Treatment | HCl salt formulation |
|---|---|
| Tmax (h) * | 3.3 (2-4) |
| Cmax (ng/mL) | 6540 ± 920 |
| Apparent T1/2 (h) | 5.0 ± 1.4 |
| AUC0-48 h(ng · h/mL) | 51600 ± 7060 |
| AUCinf (ng · h/mL) | 51800 ± 7180 |
| AUCinf/dose (ng · h/mL)/mg | 3450 ± 479 |

* Tmax given as mean and range

The following observations were made:
1. There was a 1.6-fold higher exposure (AUCinf, 51800 vs 32000 ng·h/mL) with hydrochloride salt formulation as compared with the solid dispersion formulation taken without a meal.
2. The hydrochloride salt formulation and the solid dispersion formulation are expected to provide comparable bioavailability in humans.

The invention claimed is:

1. Crystalline form A of asciminib hydrochloride characterized by having an x-ray powder diffraction pattern comprising reflections at 2-Theta angles of 12.6±0.2°, 18.9±0.2° and 20.9±0.2°, when measured at a temperature in the range of from 20 to 25° C. with Cu-Kalpha$_{1,2}$ radiation having a wavelength of 0.1541Å.

2. The crystalline form according to claim 1 characterized by having an x-ray powder diffraction pattern comprising reflections at 2-Theta angles of 12.6 ±0.2°, 17.0 ±0.2°, 18.9 ±0.2°, 20.9 ±0.2° and 32.5 ±0.2°, when measured at a temperature in the range of from 20 to 25° C. with Cu-Kalpha$_{1,2}$ radiation having a wavelength of 0.1541Å.

3. The crystalline form according to claim 1 characterized by having an x-ray powder diffraction pattern comprising at least three 2 theta values selected from the group consisting of 8.5° ±0.2°, 9.5° ±0.2°, 11.8° ±0.2°, 12.3° ±0.2°, 12.6° ±0.2°, 13.9° ±0.2°, 14.8° ±0.2°, 15.9° ±0.2°, 16.5° ±0.2°, 17.0° ±0.2°, 17.6° ±0.2°, 18.9° ±0.2°, 19.1° ±0.2°, 19.8° ±0.2°, 20.4° ±0.2°, 20.9° ±0.2°, 21.2° ±0.2°, 22.4° ±0.2°, 22.7° ±0.2°, 23.9° ±0.2°, 24.3° ±0.2°, 24.8° ±0.2°, 25.0° ±0.2°, 25.9° ±0.2°, 26.8° ±0.2°, 27.0° ±0.2°, 28.3° ±0.2°, 28.6° ±0.2°, 28.9° ±0.2°, 29.8° ±0.2°, 30.5° ±0.2°, 31.3° ±0.2°, 31.5° ±0.2°, 31.8° ±0.2°, 32.1° ±0.2°, 32.5° ±0.2°, 32.9° ±0.2°, 33.6° ±0.2°, 34.0° ±0.2°, 34.6° ±0.2°, 35.0° ±0.2°, 35.6° ±0.2°, 36.3° ±0.2° and 38.8° ±0.2°, when measured at a temperature in the range of from 20 to 25° C. with Cu -Kalpha$_{1,2}$ radiation having a wavelength of 0.1541Å.

4. The crystalline form according to claim 1 characterized by having a differential scanning calorimetry curve comprising an endothermic peak having an onset temperature of 90° C., when measured at a heating rate of 2° C/min.

5. The crystalline form according to claim 1 characterized by having a thermogravimetric analysis curve showing a mass loss of not more than 3.3 weight % based on the weight of the crystalline form, when heated from 30 to 300° C. at a rate of 20° C/min.

6. The crystalline form according to claim 1 characterized by having an x-ray powder diffraction pattern comprising at least four 2 theta values selected from the group consisting of 8.5° ±0.2°, 9.5° ±0.2°, 11.8° ±0.2°, 12.3° ±0.2°, 12.6° ±0.2°, 13.9° ±0.2°, 14.8° ±0.2°, 15.9° ±0.2°, 16.5° ±0.2°, 17.0° ±0.2°, 17.6° ±0.2°, 18.9° ±0.2°, 19.1° ±0.2°, 19.8° ±0.2°, 20.4° ±0.2°, 20.9° ±0.2°, 21.2° ±0.2°, 22.4° ±0.2°, 22.7° ±0.2°, 23.9° ±0.2°, 24.3° ±0.2°, 24.8° ±0.2°, 25.0° ±0.2°, 25.9° ±0.2°, 26.8° ±0.2°, 27.0° ±0.2°, 28.3° ±0.2°, 28.6° ±0.2°, 28.9° ±0.2°, 29.8° ±0.2°, 30.5° ±0.2°, 31.3° ±0.2°, 31.5° ±0.2°, 31.8° ±0.2°, 32.1° ±0.2°, 32.5° ±0.2°, 32.9° ±0.2°, 33.6° ±0.2°, 34.0° ±0.2°, 34.6° ±0.2°, 35.0° ±0.2°, 35.6° ±0.2°, 36.3° ±0.2° and 38.8° ±0.2°, when measured at a temperature in the range of from 20 to 25° C. with Cu -Kalpha$_{1,2}$ radiation having a wavelength of 0.1541Å.

7. The crystalline form according to claim 1 characterized by having an x-ray powder diffraction pattern comprising at least five 2 theta values selected from the group consisting of 8.5° ±0.2°, 9.5° ±0.2°, 11.8° ±0.2°, 12.3° ±0.2°, 12.6° ±0.2°, 13.9° ±0.2°, 14.8° ±0.2°, 15.9° ±0.2°, 16.5° ±0.2°, 17.0° ±0.2°, 17.6° ±0.2°, 18.9° ±0.2°, 19.1° ±0.2°, 19.8° ±0.2°, 20.4° ±0.2°, 20.9° ±0.2°, 21.2° ±0.2°, 22.4° ±0.2°, 22.7° ±0.2°, 23.9° ±0.2°, 24.3° ±0.2°, 24.8° ±0.2°, 25.0° ±0.2°, 25.9° ±0.2°, 26.8° ±0.2°, 27.0° ±0.2°, 28.3° ±0.2°, 28.6° ±0.2°, 28.9° ±0.2°, 29.8° ±0.2°, 30.5° ±0.2°, 31.3° ±0.2°, 31.5° ±0.2°, 31.8° ±0.2°, 32.1° ±0.2°, 32.5° ±0.2°, 32.9° ±0.2°, 33.6° ±0.2°, 34.0° ±0.2°, 34.6° ±0.2°, 35.0° ±0.2°, 35.6° ±0.2°, 36.3° ±0.2° and 38.8° ±0.2°, when measured at a temperature in the range of from 20 to 25° C. with Cu -Kalpha$_{1,2}$ radiation having a wavelength of 0.1541Å.

8. The crystalline form according to claim 1 characterized by having an x-ray powder diffraction pattern similar to FIG. 8.

9. Crystalline form A of asciminib hydrochloride characterized by the following unit cell parameters from x-ray diffraction data measured at 100K:

| Space symmetry | Triclinic |
|---|---|
| Space group | P1 |
| Cell Volume (Å$^3$) | 1053.6(6) |
| Crystal Density (g/cm$^3$) | 1 |
| a (Å) | 8.203(3) |
| b (Å) | 11.116(3) |
| c (Å) | 12.627(4) |
| beta (°) | 97.711(12) |
| Z | 2. |

10. Crystalline form A of asciminib hydrochloride characterized by the following unit cell parameters from x-ray diffraction data measured at 298K:

| Space symmetry | Triclinic |
|---|---|
| Space group | P1 |
| Cell Volume (Å$^3$) | 1082.9(6) |
| Crystal Density (g/cm$^3$) | 1.491 |
| a (Å) | 8.245(3) |
| b (Å) | 11.352(4) |
| c (Å) | 12.697(4) |
| beta (°) | 97.289(18) |
| Z | 2. |

* * * * *

UNITED STATES PATENT AND TRADEMARK OFFICE
CERTIFICATE OF CORRECTION

| | | |
|---|---|---|
| PATENT NO. | : 11,407,735 B2 | Page 1 of 1 |
| APPLICATION NO. | : 16/874622 | |
| DATED | : August 9, 2022 | |
| INVENTOR(S) | : Stephanie Kay Dodd et al. | |

It is certified that error appears in the above-identified patent and that said Letters Patent is hereby corrected as shown below:

In the Claims

In Claim 9, at Column 24, Line 45, replace "Crystal Density (g/cm3)    1" with "Crystal Density (g/cm3)    1.533"

Signed and Sealed this
Thirteenth Day of September, 2022

Katherine Kelly Vidal
*Director of the United States Patent and Trademark Office*